(12) United States Patent
Mehta et al.

(10) Patent No.: US 7,431,944 B2
(45) Date of Patent: *Oct. 7, 2008

(54) DELIVERY OF MULTIPLE DOSES OF MEDICATIONS

(75) Inventors: Atul M. Mehta, Ramsey, NJ (US); Andrew L. Zeitlin, Millington, NJ (US); Maghsoud M. Dariani, Fanwood, NJ (US)

(73) Assignee: Celgene Corporation, Warren, NJ (US)

( * ) Notice: Subject to any disclaimer, the term of this patent is extended or adjusted under 35 U.S.C. 154(b) by 320 days.

This patent is subject to a terminal disclaimer.

(21) Appl. No.: 10/458,451

(22) Filed: Jun. 10, 2003

(65) Prior Publication Data

US 2004/0091532 A1  May 13, 2004

Related U.S. Application Data

(60) Continuation of application No. 09/038,470, filed on Mar. 11, 1998, now Pat. No. 6,635,284, which is a division of application No. 09/892,190, filed on Jul. 14, 1997, now Pat. No. 5,837,284, which is a continuation-in-part of application No. 08/647,642, filed on May 15, 1996, now abandoned, and a continuation-in-part of application No. 08/583,317, filed on Jan. 5, 1996, now Pat. No. 5,733,756, and application No. 08/567,131, Dec. 4, 1995, now abandoned.

(51) Int. Cl.
| | |
|---|---|
| A61K 9/50 | (2006.01) |
| A61K 9/48 | (2006.01) |
| A61K 9/54 | (2006.01) |
| A61K 9/20 | (2006.01) |
| A61K 9/22 | (2006.01) |
| A61K 9/28 | (2006.01) |
| A61K 9/36 | (2006.01) |
| A61K 9/14 | (2006.01) |
| A61K 9/16 | (2006.01) |

(52) U.S. Cl. ........................ 424/497; 424/451; 424/458; 424/462; 424/464; 424/468; 424/474; 424/480; 424/489; 424/490

(58) Field of Classification Search ................ 424/497, 424/458, 474, 468, 464, 490, 462, 494, 489, 424/480, 451
See application file for complete search history.

(56) References Cited

U.S. PATENT DOCUMENTS 2,507,631 A  5/1950  Hartmann et al. ........... 260/294

(Continued)

FOREIGN PATENT DOCUMENTS

CA  1297368  3/1992

(Continued)

OTHER PUBLICATIONS

Aoyama, T. et al., "Pharmacodynamic Modeling for Change of Locomotor Activity by Methyllphenidate in Rats," *Pharmaceutical Research*, 1997, 14(11), 1601-1606.

(Continued)

*Primary Examiner*—Humera N. Sheikh
(74) *Attorney, Agent, or Firm*—Woodcock Washburn LLP (57) ABSTRACT

Dosage forms for oral administration of a methylphenidate drug are provided. The dosage forms provide a substantially immediate dose of methylphenidate upon ingestion, followed by one or more additional doses at predetermined times. By providing such a drug release profile, the dosage forms eliminate the need for a patient to carry an additional dose for ingestion during the day. The dosage forms and methods provided are useful in administering methylphenidate and pharmaceutically acceptable salts thereof, which generally require one or more doses throughout the day.

6 Claims, 2 Drawing Sheets

U.S. PATENT DOCUMENTS

| | | | |
|---|---|---|---|
| 2,838,519 A | 6/1958 | Rometsch et al. | 260/294.3 |
| 2,957,880 A | 10/1960 | Rometsch | 546/233 |
| 4,137,300 A | 1/1979 | Sheth et al. | 424/21 |
| 4,410,700 A | 10/1983 | Rice | 546/149 |
| 4,794,001 A | 12/1988 | Mehta et al. | 424/458 |
| 4,882,166 A | 11/1989 | Graham et al. | 424/462 |
| 4,904,476 A | 2/1990 | Mehta et al. | 424/456 |
| 4,968,505 A | 11/1990 | Okada et al. | 424/400 |
| 4,986,987 A | 1/1991 | Ayer et al. | 424/473 |
| 4,992,445 A | 2/1991 | Lawter et al. | 514/279 |
| 5,104,899 A | 4/1992 | Young et al. | 514/646 |
| 5,114,946 A | 5/1992 | Lawter et al. | 514/279 |
| 5,133,974 A | 7/1992 | Paradissis et al. | 424/480 |
| 5,137,733 A | 8/1992 | Noda et al. | 424/497 |
| 5,156,850 A | 10/1992 | Wong et al. | 424/473 |
| 5,158,777 A | 10/1992 | Abramowitz et al. | 424/458 |
| 5,160,744 A | 11/1992 | Jao et al. | 424/473 |
| 5,202,128 A | 4/1993 | Morella et al. | 424/469 |
| 5,217,718 A | 6/1993 | Colley et al. | 424/449 |
| 5,223,265 A | 6/1993 | Wong | 424/473 |
| 5,229,131 A | 7/1993 | Amidon et al. | 424/451 |
| 5,232,705 A | 8/1993 | Wong et al. | 424/473 |
| 5,236,689 A | 8/1993 | Wong et al. | 424/473 |
| 5,283,193 A | 2/1994 | Yamamoto et al. | 435/280 |
| 5,284,769 A | 2/1994 | Evans et al. | |
| 5,299,121 A | 3/1994 | Brill et al. | 364/413.01 |
| 5,308,348 A | 5/1994 | Balaban et al. | 604/892.1 |
| 5,326,570 A | 7/1994 | Rudnic et al. | 424/458 |
| 5,331,000 A | 7/1994 | Young et al. | 514/570 |
| 5,362,755 A | 11/1994 | Barberich et al. | 514/649 |
| 5,375,693 A | 12/1994 | Woosley et al. | 514/317 |
| 5,391,381 A | 2/1995 | Wong et al. | 424/473 |
| 5,425,950 A | 6/1995 | Dandiker et al. | 424/480 |
| 5,449,743 A | 9/1995 | Kobayashi et al. | 528/355 |
| 5,478,573 A | 12/1995 | Eichel et al. | 424/480 |
| 5,496,561 A | 3/1996 | Okada et al. | 424/480 |
| 5,500,227 A | 3/1996 | Oshlack et al. | 424/476 |
| 5,512,293 A | 4/1996 | Landrau et al. | 424/449 |
| 5,567,441 A | 10/1996 | Chen | 424/494 |
| 5,580,578 A | 12/1996 | Oshlack et al. | 424/468 |
| 5,593,694 A | 1/1997 | Hayashida et al. | 124/468 |
| 5,639,476 A | 6/1997 | Oshlack et al. | 424/468 |
| 5,672,360 A | 9/1997 | Sackler et al. | 424/490 |
| 5,733,756 A | 3/1998 | Zeitlin et al. | 435/122 |
| 5,773,478 A | 6/1998 | Richards et al. | 514/649 |
| 5,837,284 A | 11/1998 | Mehta et al. | 424/459 |
| 5,874,090 A | 2/1999 | Baker et al. | 424/400 |
| 5,908,850 A | 6/1999 | Zeitlin et al. | 514/315 |
| 5,922,736 A * | 7/1999 | Dariani et al. | |
| 5,936,091 A | 8/1999 | Khetani et al. | 546/233 |
| 5,965,734 A | 10/1999 | Ramaswamy et al. | 546/233 |
| 6,031,124 A | 2/2000 | Fox et al. | 560/37 |
| 6,113,879 A | 9/2000 | Richards et al. | 424/9.1 |
| 6,121,453 A | 9/2000 | Zavareh | 546/238 |
| 6,127,385 A | 10/2000 | Midha et al. | 514/317 |
| 6,217,904 B1 | 4/2001 | Midha et al. | 424/468 |
| 6,221,883 B1 | 4/2001 | Baldessarini et al. | 514/317 |
| 6,228,398 B1 | 5/2001 | Devane et al. | 424/484 |
| 6,242,464 B1 | 6/2001 | Harris et al. | 514/317 |
| 6,255,325 B1 | 7/2001 | Dariani et al. | 514/317 |
| 6,344,215 B1 | 2/2002 | Bettman et al. | 424/459 |
| 6,355,656 B1 | 3/2002 | Zeitlin et al. | 514/317 |
| 6,359,139 B1 | 3/2002 | Khetani et al. | 546/233 |
| 6,395,752 B1 | 5/2002 | Midha et al. | 514/317 |
| 6,441,178 B2 | 8/2002 | Zavareh et al. | 546/238 |
| 6,468,504 B1 | 10/2002 | Richards et al. | 424/9.1 |
| 6,486,177 B2 | 11/2002 | Zeldis et al. | 514/317 |
| 6,528,530 B2 | 3/2003 | Zeitlin et al. | 514/317 |
| 6,531,489 B2 | 3/2003 | Harris et al. | 514/317 |
| 6,602,887 B2 | 8/2003 | Dariani et al. | 517/317 |
| 6,635,284 B2 * | 10/2003 | Mehta et al. | |
| 6,730,325 B2 | 5/2004 | Devane et al. | 424/489 |
| 6,962,997 B1 | 11/2005 | Khetani et al. | 546/233 |
| 7,115,631 B2 | 10/2006 | Zeldis et al. | 514/317 |
| 2002/0019535 A1 | 2/2002 | Zavareh et al. | 546/227 |
| 2002/0032335 A1 | 3/2002 | Langston et al. | 546/238 |
| 2002/0103162 A1 | 8/2002 | Epstein et al. | |
| 2002/0132793 A1 | 9/2002 | Epstein et al. | 514/79 |
| 2003/0049205 A1 | 3/2003 | Richards et al. | 424/9.1 |
| 2003/0105134 A1 | 6/2003 | Harris et al. | 514/317 |
| 2003/0170181 A1 | 9/2003 | Midha | 424/10.4 |

FOREIGN PATENT DOCUMENTS

| | | |
|---|---|---|
| CA | 2 368 367 | 10/2000 |
| CA | 2 376 215 A1 | 12/2001 |
| CA | 2 223 643 C | 12/2003 |
| EP | 0 636 366 A2 | 2/1995 |
| EP | 0 885 191 B1 | 1/2002 |
| EP | 0 889 874 B1 | 1/2002 |
| EP | 0 841 928 B1 | 9/2002 |
| EP | 0 879 228 B1 | 10/2002 |
| EP | 0 958 281 B1 | 3/2004 |
| FR | 2 635 460 | 9/1994 |
| GB | 589625 | 1/1945 |
| GB | 788226 | 12/1957 |
| GB | 878167 | 9/1961 |
| RU | 466229 | 4/1975 |
| WO | WO93/05769 | 1/1993 |
| WO | 96/41617 A1 | 12/1996 |
| WO | WO97/03671 | 2/1997 |
| WO | WO97/03672 | 2/1997 |
| WO | WO97/03673 | 2/1997 |
| WO | WO97/27176 | 7/1997 |
| WO | WO97/28124 | 8/1997 |
| WO | WO97/32851 | 9/1997 |
| WO | WO97/35836 | 10/1997 |
| WO | WO98/06380 | 2/1998 |
| WO | WO98/23263 | 4/1998 |
| WO | WO98/25902 | 6/1998 |
| WO | WO98/31668 | 7/1998 |
| WO | WO98/14168 | 9/1998 |
| WO | WO99/62496 | 12/1999 |
| WO | WO 00/74680 A1 | 12/2000 |
| WO | WO 01/43730 A3 | 6/2001 |
| WO | 2004/026258 A2 | 4/2004 |

OTHER PUBLICATIONS

Aoyama, T. et al., "Pharmacokinetics and pharmacodynamics of methylphenidate enantiomers in rats," *Psychopharmacology*, 1996, 127, 117-122.

Aoyama, T., et al., "Nonlinear kinetics of threo-methylphenidate enantiomers in a patient with narcolepsy and in healthy volunteers," *Eur. J. Clin. Pharmacol.*, 1993, 44, 79-84.

Barkley, R. A., et al., "The adolescent outcome of hyperactive children diagnosed by research criteria: I. An 8-year prospective follow-up study," *J. Am. Acad. Adolesc. Psychiatry.*, 1990, 29(4), 546-557.

Baughman, Jr., F. A., "Treatment of Attention-Deficit/Hyperactivity Disorder," *JAMA.*, Apr. 28, 1999, 218(16), 1490-1491.

Bruera, E., and Neumann, C. M., "The uses of psychotropics in symptom management in advanced cancer," *Pscyho-Oncology.*, 1998, 7, 346-358.

Carey, W. B., "What the multimodal treatment study of children with attention-deficit/hyperactivity disorder did and did not say about the use of methylphenidate for attention deficits," *Pediatrics*, 2000, 863-864.

Coyle, J. T., "Psychotic drug use in very young children," *J. Am. Med. Assn.*, 2000, 283(8), 1059-1060.

Davids, E. et al., "Stereoselective effects of methylphenidate on motor hyperactivity in juvenile rats induced by neonatal 6-hydroxydopamine lesioning," *Psychopharmacology*, 2002, 160, 92-98.

Ding, Y.-S. et al., "Chiral drugs: comparison of the pharmacokinetics of [11C]d-threo and *l-threo*-methylphenidate in the human and baboon brain," *Psychopharmacology*, 1997, 131, 71-78.

Ding, Y.-S. et al., "Is the L-threo Enantiomer of Methylphenidate (Ritalin) Inactive in the Brain when the Drug is Given Orally?" *ACNP 41st Annual Meeting*, Dec. 8-12, 2002, Scientific Abstract No. 119.

Garland, E. J., "Pharmacotherapy of adolescent attention deficit hyperactivity disorder: challenges, choices and caveats," *J. Psychopharmacology.*, 1998, 12(4), 385-395.

Golden, G. S., "Role of attention deficit hyperactivity disorder in learning disabilities," *Seminars in Neurology.*, 1991, 11(1), 35-41.

Goldman, L. S., et al., "Diagnosis and treatment of attention-deficit/hyperactivity disorder in children and adolescents," *J. Am. Med. Assn.*, 1998, 279(14), 1100-1107.

Jadad, A. R., et al., "Review: Pharmacologic interventions are more effective than non-pharmacologic for attention-deficit hyperactivity disorder," *Therapeutics, ACP Journal Club.*, Nov./Dec. 2000, 110.

Jensen, P. S., et al., "Are stimulants over-prescribed? Treatment of ADHD in four U.S. communities," *J. Am. Acad. Adolesc. Psychiatry.*, 1999, 37(7), 797-804.

Jonkman, L. M. et al., "Differences in plasma concentrations of the D- and L-*threo* methylphenidate enantiomers in responding and non-responding children with attention-deficit hyperactivity disorder," *Psychiatry Research*, 1998, 78, 115-118.

Kimko, H.C. et al., "Pharmacokinetics and Clinical Effectiveness of Methylphenidate," *Clin Pharmacokinet*, Dec. 1999, 37(6), 457-470.

LeFever, G. B., et al., "The extent of drug therapy for attention deficit-hyperactivity disorder among children in public schools," *American Journal of Public Health*, (Sep. 1999), (89)9, 1359-1364.

Lin, J. H., and Lu, A. H., "Role of pharmacokinetics and Metabolism in drug discovery and development," *Pharmacological Reviews*, 1997, 49(4), 403-449.

Llana, M. E. and Crismon, M. L., "Methylphenidate: increased abuse or appropriate use?" *J. Amer. Pharmaceut. Assn.*, 1999, 39(4), 526-530.

MacDougall, M. K., et al., "Symptom control in the pregnant cancer patient," *Seminars in Oncology.*, 2000, 27(6), 704-711.

McCarthy, M., "USA to improve care of children with ADHD," *The Lancet*, 2000, 355, 1161.

Mehta, M. A., et al., "Methylphenidate enhances working memory by modulating discrete frontal and parietal lobe regions in the human brain," *J. Neurosci.*, 2000, 20RC65: (1-6).

Modi, N. B. et al., "Dose-Proportional and Stereospecific Pharmacokinetics of Methylphenidate Delivered Using an Osmotic, Controlled-Release Oral Delivery System," *J Clin Pharmacol*, 2000, 40, 1141-1149.

Chapin, R. et al., "*Methylphenidate hydrochloride*," Environmental Health Perspectives, 1997, 105 (supp 1), 319-320.

Patrick, K.S. et al., "Pharmacology of Methylphenidate, Amphetamine Enantiomers and Pemoline in Attention-Deficit Hyperactivity Disorder," *Human Psychopharmacology*, 1997, 12, 527-546.

Patrick K.S. et al, "The Absorption Of Sustained-Release Methylphenidate Formulations Compared To An Immediate-Release Formulation" Biopharmaceutics And Drug Disposition, Wiley, Chichester, US, vol. 10, No. 2, 1989, pp. 165-171.

Quinn, D.M.P., "Methylphenidate: The Role of the d-Isomer," undated, Department of Psychiatry, College of Medicine, University of Saskatchewan, Saskatoon, Saskatchewan, Canada, 369-373.

Rouhi, A.M, "Chirality at Work," *C&EN*, May 5, 2003, 56-61.

Schweitzer J. B., et al., "Attention deficit hyperactivity disorder," *Adv. Pathophysiol. And Treat. Psychiatric Disorders: Implications for Internal Med.*, 2001, 85(3), 757-777.

Shader R.I. et al., "Population Pharmacokinetics of Methylphenidate in Children with Attention-Deficit Hyperactivity Disorder," *J Clin Pharmacol*, 1999, 39, 775-785.

Spencer, T., et al., "Pharmacotherapy of attention-deficit hyperactivity disorder across the life cycle," *J. Am. Acad. Adolesc. Psychiatry.*, 1996, 35(4), 409-432.

Srinivas, N.R. "Role of Stereoselective Assays in Bioequivalence Studies of Racemic Drugs: Have We Reached a Consensus?" *J Clin Pharmacol*, Feb. 2004, 44, 115-119.

Srinivas, N.R., et al., "Enantiomeric Drug Development: Issues, Considerations, and Regulatory Requirements," *Journal of Pharmaceutical Sciences*, Sep. 2001, 90(9), 1205-1215.

Stein, M. A., et al., "Methylphenidate dosing: Twice daily versus three times daily," *Pediatrics.*, 1996, 98(4), 748-756.

Swanson, J. M., et al., "Acute tolerance to methylphenidate in the treatment of attention deficit hyperactivity disorder in children," *Clin. Pharmacology and Therapeut.*, 1999, 66(3), 295-305.

Swanson, J. M., et al., "Analog classroom assessment of Adderall in children with ADHD," *J. Am. Acad. Adolesc. Psychiatry.*, 1998, 37(5), 519-525.

Taylor, M. A., "Attention-deficit hyperactivity disorder on the frontlines: Management in the primary care office," *Comp. Ther.*, 1999, 25(6/7), 313-325.

Teo, S. K., et al., "A 90-day oral gavage toxicity study of D-methylphenidate and D,L-methylphenidate in beagle dogs," *Internat. J. Toxicol.*, May/Jun. 2003, 22, 215-226.

Teo, S. K., et al., "D-Methylphenidate and D,L-methylphenidate are not developmental toxicants in rats and rabbits," *Birth Defects Research (Part B).*, Apr. 2003, 68, 162-171.

Teo, S. K., et al., "D-Methylphenidate is non-genotoxic in *in vitro* and *in vivo* assays," *Mutation Research.*, May 9, 2003, 537, 67-69.

Teo, S. K., et al., "Neurobehavioral effects of racemic *threo*-methylphenidate and its D and L enantiomers in rats," *Pharmacology, Biochemistry, and Behavior*, Feb. 2003, 74, 747-754.

Teo, S., et al., "A 90-day oral gavage toxicity study of D-methylphenidate and D,L-methylphenidate in Sprague-Dawley rats," *Toxicology.*, 2002, 179, 183-196.

Teo, S.K. et al., "The perinatal and postnatal toxicity of D-methylphenidate and D,L-methylphenidate in rats," *Reproductive Toxicology*, 2002, 16, 353-366.

Thai, D.L., et al., "Comparative Pharmacokinetics and Tissue Distribution of the *d*-enantiomers of Para-substituted Methylphenidate Analogs," *Drug Metabolism and Disposition*, 1999, 27(6),.

Thomson, M.R. et al., "Enantioselective Transesterification of Methylphenidate to Ethylphenidate After Coadministration with Ethanol," *Thirty-First Annual ACCP Meeting Abstracts*, 2002, Abstract No. 80.

Tripp, G. and Alsop, B., "Sensitivity to reward frequency in boys with attention deficit hyperactivity disorder," *J. Clin. Child Psychology.*, 1999, 28(3), 366-375.

Volkow, N. D. et al., "Mechanism of action of methylphenidate: Insights from PET imaging studies," *Journal of Attention Disorders*, 2002, 9(Suppl. Jan. 2002), S-31-S43.

Volkow, N.D. et al., "Effects of Methylphenidate on Regional Brain Glucose Metabolism in Humans: Relationship to Dopamine $D_2$ Receptors," *Am J Psychiatry*, Jan. 1997, 154(1), 50-55.

Volkow, N.D. et al., "Temporal relationships between the pharmacokinetics of methylphenidate in the human brain and its behavioral and cardiovascular effects," *Psychopharmacology*, 1996, 123, 26-33.

Ward, M. F., et al., "The Wender Utah rating scale: an aid in the retrospective diagnosis of childhood attention deficit hyperactivity disorder," *Am. J. Psychiatry.*, 1993, 150(6), 885-890.

Weiler, M. D., et al., "Mother and Teacher Reports of ADHD Symptoms: DSM-IV Questionnaire Data," *J. Am. Acad.Child Adolesc. Psychiatry*, Sep. 1999, 38(9), 1139-1147.

Zametkin, A. J. and Ernst, M., "Problems in the management of attention-deficit/hyperactivity disorder," *New. Eng. Jour. Med.*, 1999, 340(1), 40-46.

Zito, J. M., et al., "Trends in the prescribing of psychotropic medications to preschoolers," *J. Am. Med. Assn.*, 2000, 283(8), 1025-1030.

Aoyama, T., et al., Gas chromatographic-mass spectrometric analysis of *threo*-methylphenidate enantiomers in plasma, *J. Chromatography*, 1989, 494, 420-423.

Axten, J.M., et al., "A stereoselective synthesis of *dl-threo*-methylphenidate: preparation and biological evaluation of novel analogues," *J. Org. Chem.*, 1998, 63, 9628-9629.

Axten, J.M., et al., "Enantioselective synthesis of $_D$-*threo*-methylphenidate," *J. Am. Chem. Soc.*, 1999, 121, 6511-6512.

Davies, H.M.L., et al., "Highly regio-, diastereo-, and enantioselective C—H insertions of methyl aryldiazoacetates into cyclic N-bocprotected amines asymmetric synthesis of novel $C_2$-symmetric amines and *threo*-methylphenidate," *J. Am. Chem. Soc.*, 1999, 121, 6509-6510.

Deutsch, H.M., et al., "Synthesis and pharmacology of potential cocaine antagonists. 2. Structure-activity relationship studies of aromatic ring-substituted methylphenidate analogs," *J. Med. Chem.*, 1996, 39, 1201-1209.

Dirksen, SJ.H., et al., "A postmarketing clinical experience study of Metadate® CD," *Curr. Med. Res. and Opinion*, 2002, 18(7), 371-380.

Hubbard, J.W., et al., "Enantioselective aspects of the disposition of *dl-threo*-methylphenidate after the administration of a sustained-release formulation to children with attention deficit-hyperactivity disorder," *J. of Pharm. Sci.*, 1989, 78(11), 944-947.

Lim, H.K., "Enantiomeric resolution of *dl-threo*-methylphenidate, U.S.P. (Ritalin®), by high-performance liquid chromatography," *J. of Chromatography*, 1985, 328, 378-386.

Matsumura, Y., et al., "A convenient method for synthesis of enantiomerically enriched methylphenidate from *N*-methoxycarbonylpiperidine," *Organic Letters*, 1999, 1(2), 175-178.

Naito, T., et al., "Rearrangement of sulfonamide derivatives. V. Syntheses of methyl α-phenyl-2- and 4-piperidineacetate," *Chem. Pharm. Bull.*, 1964, 12(5), 588-590.

Panizzon, Leandro, "Preparation of pyridyl- and piperidylarylacetonitriles and some derivatives.", *Helvetica Chimica Acta*, 1944, 27, 1748-1756.

Prashad, M., et al., "Enzymatic resolution of (±)-*threo*-methylphenidate," *Tetrahedron: Asymmetry*, 1998, 9, 2133-2136.

Prashad, M., et al., "Enantioselective synthesis of (2S,2'R)-*erythro*-methylphenidate," *Tetrahedron: Asymmetry*, 1999, 10, 3479-3482.

Prashad, M., "The first enantioselective synthesis of (2,R,2',R)-threo(+)-methylphenidate hydrochloride," *J. Org. Chem.*, 1999, 64, 1750-1753.

Rochdi, M., et al., "Dose-proportional pharmacokinetics of a methylphenidate extended-release capsule," *Int. J. of Clin. Pharma. And Theraps.*, 2004, 42(5), 285-292.

Thai, D.I., et al., "Asymmetric synthesis and pharmacology of methylphenidate and its para-substituted derivatives," *J. Med. Chem.*, 1998, 41, 591-601.

Panizzon, L., Preparation of pyridyl and piperidyl arylacetonitriles and of a number of conversion products (Part 1), *Helvetica Chimica Acta*, 1944, 27, 1748-1756 (translation; previously cited with English abstract).

Eckerman, D.A., et al., "Enantioselective behavioral effects of *threo*-methylphenidate in rats," *Pharmacology Biochem. & Behav.*, 1991, 40, 875-880.

Srinivas, N.R., et al., "Enantioselective pharmacokinetics and pharmacodynamics of *dl-threo*- methylphenidate in children with attention deficit hyperactivity disorder," *Clin. Pharmacol. Ther.*, 1992, 52, 561-568.

Angrist, et al., *J. of Clin. Phsychopharmacol.*, 1992, 12, 268-272.

Aoyama, et al., "Pharmacolinetics and pharmacodynamics of (+)-threo-methylphenidate enantiomer in patients with hypersomnia," *Clin. Pharmacol. Ther.*, 1994, 55(3), 270-276.

Barkley, et al., *Pediatrics*, 1990, 86, 184-192.

Barkley, et al., *Pediatrics*, 1991, 87, 519-531.

Bowden, et al., "Reactions of carbonyl compounds in basic solutions the alkaline hydrolysis of N-alkyl-N-methylacetamides," *J. Chem. Soc. Perkin Trans.*, 1990, 12, 2111-2116.

Brown, C., "Pharmacological action and drug development," *Chirality in Drug Design and Synthesis, Academic Press, Inc.*, 1990, 4-7.

Brown, G., "The use of methylphenidate for cognitive decline associated with HIV disease," *Int'l J. Psychiatry Med.*, 1995, 25(1), 21-37.

Corey, et al., "A new synthetic approach to the penicillins," *J. Amer. Chem. Soc.*, 1965, 87(11), 2518-2519.

Ding, et al., "Cis- and trans-axetidin-2-ones from nitrones and copper acetylide," *J. Chem. Soc. Perkin*, 1976, 22, 2382-2386.

Douzenis, et al., "Phychiatric disorder in HIV disease: description of 200 referrals to a liaison psychiatry service," *Proc. 7th Int'l Conf. AIDS*, 1991, 215, M.B. 2135 Summary.

Earle, et al., "Synthesis and hydrolysis of some fused-ring β-lactams," *J. Chem. Soc.*, 1969, 2093-2098.

Golinko Prog. *Neur-Psychopharmacol. & Biol. Phsychiat.*, 1984, 8, 1-8.

Greenhill, L., "Attention-deficit hyperactivity disorder," *Child & Adol. Psych. Clin. N.A.*, 1995, 4(1), 123-168.

Greenhill, "Pharmacologic treatment of attention deficit hyperactivity disorder," 1992, 15(1), 1-27.

Holmes, et al., "Psychostimulant response in aids-related complex patients," *J. Clin. Psychiatry*, Biosis Abstract No. 87129969, 50(1), 5-8.

Hou, J.P., et al., "Beta-lactam antibiotics: their physicochemical properties and biological activities in relation to structure," *J. Pharm. Sci.*, 1971, 60(4), 503-532.

Klibanov, A.M., "Asymmetric transformations catalyzed by enzymes in organic solvents," *Acc. Chem. Res.*, 1990, 23, 114-120.

Moll, F., "Darstellung von 1-Aza-bicyclo [4.2.0] octan-2-on," *Naturforsch Teil B.*, 1966, 21, 297.

Navia, et al., "The AIDS dementia complex: I. Clinical features," *Annals of Neurology*, 1986, 19, 517-524.

Patrick, et al., "Pharmacology of the enantiomers of threo-methylphenidate," *J. Pharmacol. & Exp. Terhap.*, 1987, 241, 152-158.

Rieder, et al., "Diagnosis of sulfonamide hypersensitivity reactions by in-vitro "rechallenge" with hydroxylamine metabolites," *Ann. Intern. Med.*, 1989, 110, 286-289.

Scott, "Stereoisomers and drug toxicity," *Drug Safety*, 1993, 8(2), 149-159.

Srinivas, et al., "Enantioselective pharmacolinetics and pharmacodynamics of racemic threo-methylphenidate in children with attention deficit hyperactivity disorder," *Clin. Pharmacol. Ther.*, Biosis Abstract No. 95066168, 52(2), 561-568, 1992.

Srinivas, et al., "Enantiomeric gas chromatography assay with electron capture detection for d-ritalinic acid in plasma," *J. Chromatagraph*, 1990, 530, 327-336.

Srinivas, et al., "Sterioselective disposition of methylphenidate in children with attention deficit disorder," *J. Pharmacol. Exp. Ther.*, 1987, 241, 300-306.

Srinivas, et al., "Enantioselective pharmacokinetics of dl-threo-methylphenidate in humans," *Pharmacol. Res.*, 1993, 10(1), 14-21.

Staal, et al., "Glutathione deficiency and human immunodeficiency virus infection," *Lancet*, 1992, 339, 909-912.

Uetrecht, et al., "Idiosyncratic drug reactions: possible role of reactive metabolites generated by leukocytes," *Pharmacol. Res.*, 1989, 6(4), 265-273.

White, et al., "Methylphenidate as a treatment for depression in acquired immunodeficiency syndrome: an n-of-1 trial," *J. Clin. Phsychiatry*, 1992, 53(5), 153-156.

Physicians's Desk Reference, 46th Ed., "Ritalin SR", 1992, 880-881.

Challman, T.D., et al., "Methylphenidate: its pharmacology and uses," *Mayo Clin Proc.*, 2000, 75, 711-721.

Sarhill, N., et al., "Methylphenidate for fatigue in advanced cancer: a prospective open-label pilot study," *Am. J. of Hospice & Palliative Care*, 2001, 18(3), 187-192.

Aoyama et al., Kinetic Analysis of Enantiomers of threo-Methylophenidate and Its Metabolite in two Healthy Subjects after Oral Administration as Determined by a Gas Chromatographic-Mass Spectrometric Method, 1990, vol. 79, No. 6, pp. 465-469.

Arnold, L. E. et al., "A Double-Blind, Placebo-Controlled Withdrawal Trial of Dexmethylphenidate Hydrochloride in Children with Attention Deficit Hyperactivity Disorder," 2004, *J. Am. Child Adolesc. Psychopharmacol.* 14(4):542-554.

Ding, Y-S. et al., "Brian Kinetics of Methylphenidate (Ritalin) Enantiomers After Oral Administration," *Synapse*, Sep. 2004, 53, 168-175.

Jaffe, P., "Will the real Ritalin please stand up?," *A Quarterly Newsletter by ad for Adults who have Attention Deficit Disorder*, 1992, Issue #10, 3 pages.

Jarvi et al., "Bioequivalence of Methylphenidate Tablets," Abstract PPDM 8169, *Pharmaceutical Research* vol. 7, No. 9, 1990, 2 pages.

Markowitz, J. S., et al., "Advances in the pharmacotherapy of attention-deficit-hyperactivity disorder: focus on methyl phenidate formulations," *Pharmacotherapy*, Oct. 2003, 23(10), 1281-1299.

Meyer, et al., "Bioequivalence of Methylphenidate Immediate-Release Tables Using a Replicated Study Design to Characterize Intrasubject variability," *Oharmaceutical Research*, vol. 17, No. 4, 2000, 381-384.

Patrick et al., "Distribution of Methylphenidate and P-Hydroxymethylphenidate in Rats," *Journal od Pharmacology and Experimental Therapeutics*, 1984, vol. 231, No. 1, 61-65.

Patrick, K. S. et al., "New methylphenidate formulations for the treatment of attention-deficit/hyperactivity disorder," *Expert Opin, Drug Deliv.*, 2005, 2(1), 121-143.

Patrick, K.S. et al., Poster Abstract 267, "Synthesis, Phamacology and Human Metabolic Formation of Ethylphenidate: the Transesterification Product of Methylphenidate and Ethanol," *The 56th Southwest Regional Meeting* 2004, Nov. 10-13, 2004, 2 pages.

Quinn, D. et al., "Comparative pharmacodynamics and plasma concentration of d-thero-methylphenidate hydrochloride after single doses of d-thero-methylphenidate hydrochloride and d,l-thero-methylphenidate hydrochrloride in a double-blinde, placebo-controlled, crossover laboratory school study in children with attention-deficit/hyperectivity disorder," Nov. 2004, *J. Am. Chil Adolesc. Psychiatry* 43(11):1422-1429.

Silva, R. et al., "Open -Label Study of Dexmethylphenidate Hydrochloride in Children and Adolescents with Attention Deficit Hyperactivity Disorder," 2004, *J. child Adolesc. Psychopharmacol.* 14(4):555-563.

Volkow, N.D. et al., "Evidence That Methylphenidate Enhances the Sliency of a Mathematical Task by Increasing Dopamine in the Human Brain," *Am. J. Psychiatry*, Jul. 2004, 161(7), 1173-1180.

Weiss, M., et al., "A post hoc analysis of d-thero-methylphenidate hydrochloride (Focalin) versus d,l-thero-methylphenidate hydrochloride (Ritalin)," *J. Am. Acad. Adolesc. Psychiatry*, Nov. 2004, 43(11), 1415-1421.

Wigal, S., et al., "A double-blind, placebo-controlled trial of dexmethylphenidate hydrochloride and d,l-threo-methylphenidate hydrochloride in children with attention-deficit/hyperactivity disorder," *J. Am. Acad. Adolesc. Psychiatry*, Nov. 2004, 43(11), 1406-1414.

Amended Answer and Counterclaims of Defendant Teva Pharmaceuticals USA, Inc., filed Nov. 9, 2005, Civil Action No. 04-4030(SRC), *Celgene Corporation, Novartis Pharmaceuticals corporation and Novartic Pharma AG v. Teva Pharmaceuticals USA, Inc.* Subject to Protective Order.

Study 97-M-01, Clinical Study Report, Mar. 10, 1998, Comparative Pharmacokinetics, Pharmacodynamics, and Safety of Single Doses of d-threo-Methy;phenidate Hydrochloride and dl-threo-Methylphenidate Hydrochloride in Children With Attention Deficit/Hyperactivity Disorder. Subject To Protective Order.

"Attention-deficit and disruptive behavior disorders: Attention-deficit/hyperactivity disorder," American Psychiatric Association, Diagnostic and Statistical Manual of Mental Disorders, *Fouth Ed.* (*DSM-IV*) Washington, DC, 1994, 78-85.

Al Abwal, H. et al., "The effects of methylphenidate (MP) on Narcotic-induced Cognitive Failure (MICF)," *Am. Soc. Clin. Oncology*, 27th Annual Meeting, May 19, 21, 1991, 1385, 1992, vol. 11, p. 397.

Avis, K.E., "Parental Preparations," *Remington's Pharmaceutical Sciences, 16th Ed.*, Osol, A. (Ed.), *Mack Publishing Co.*, 1980, 1463-1487.

Berrang, B. et al., "Enantiomeric alpha aminopropiophenones (cathinone): preparation and investigation," *J. Org Chem.*, 1982, 47(13), 2643-2647.

Brown, T.E., "Emerging understandings of attention-deficit disorders and comorbidities," *Attention-Deficit Disorders and Comorbidities in Children, Adolescents, and Adults*, American Psychiatric Press, Inc., 2000, Chapter1, 3-55.

Bruera, E., et al., "Methylphenidate associates with narcotics for the treatment of cancer pain," *Cancer Treat. Resp.*, 1987, 71(1), 67-70.

Bruera, E., et al., "Narcotics plus methylphenidate (ritalin) for advanced cancer pain," *Am. J. Nursing, Pain and Symptom Counsult*, Nov. 1988, 1665-1666.

Bruera, E., et al., "Neuropsychological effects of methylphenidate in patients receiving a continuous infusion of narcotics for cancer pain," *Pain*, 1992, 48, 163-166.

Bruera, E., et al., "Overwhelming fatigue in advanced cancer," *Am. J. Nursing, Pain Consult*, Jan. 1988, 99-100.

Bruera, E., et al., "The use of methylphenidate in patients with incident cancer pain receiving regular opiates, A preliminary report," *Pain*, ISSN 0304-3959, Jul. 1992, 50(1), 75-77.

Bruera, E., et al., "Use of methylphenidate as an adjuvant to narcotic analgesics in patients with advanced cancer," *J. Pain and Symptom Management*, Mar. 1989, 4(1), 3-6.

Cella, D.F., et al., "The functional assessment of cancer therapy scale: development and validation of the general measure," *J. clin, Oncol.*, 1993, 11(3), 570-579.

Drimmer, E.J., et al., "Desipramine and methylphenidate combination treatment for depression: case report," *Am. J. pf Psychiatry*, 1983, 140(2), 241-242.

Faust, D., et al., "The development and initial validation of a sensitive bedside cognitive Screening test," *J. Nerv. Ment. Dis.*, 1989, 177(1), 25-31.

Feng, Z. et al., "Molecular determinants of the paltelet aggregation inhibitory activity of carbomaoylpiperidines," CA 117:111440, 1992.

Fernandez, F., et al., "Methylphenidate for depressive disorders in cancer patients," *Psychosomatics*, Sep. 1987, 28(9), 455-461.

Fernandez, F., et al., "Methylphenidate treatment for patients with head and neck cancer," *Head and Neck Surgery*, Mar./Apr. 1986, 8(4), 296-300.

Ferris, R.M., et al., "A comparison of the capacities of isomers of amphetamine, deoxypipradrol and methylphenidate to inhibit the uptake of tritiated catecholamines into rat cerebral cortex slices, synaptosomal preparations of rat cerebral cortex, hypothalamus and striatum and into adrenergic nerves of rabbit aorta," *J. of Pharmacology & Experimental therapeutics*, 1972, 181(3), 407-416.

Ferris, R.M., et al., "Comparison of the effects of the isomers of amphetamine, methylphenidate and deoxypipradrol on the uptake of l-[$^3$H]norepinephrine and [$^3$H]dopamine by synaptic cesicles from rat whole brain, striatum and hypothalamus," *J. of Pharmacology & Experimental Therapeutics*, 1979, 210(3), 422-428.

Folstein, S.E., et al., "Minimental state": a practical method for grading the cognitive state of patients for the clinician, *J. Psychiarty res.*, 1975, 12, 189-198.

Grob, C.S., et al., "Suspected adverse methylphenidate-imipramine interactions in children," *J. of Develop. & Behav. Pediatrics*, 1986, 7(4), 265-267.

Hales, R.E., et al., "Psychopharmacologic issues in the diagnosis and treatment of organic mental disorders," *Psychia. Clinics of North America*, Dec. 1984, 7(4), 817-829.

Jursic, B. S., et al., "Determination of enantiomeric composition of 1-phenyl-2(2-piperidinyl-acetamide. A Routine Method for Evaluation of Enantiomeric purity of Primary Amides," *Tetrahedron: asymmetry*, 1994, 5(9), 1711-1716.

KAdouch, et al., *Neuropsychobiology*, 1977, 3(4), 250-255, HCAPLUS Abstract 88:115433.

Macleod, A.D., "Methylphenidate in terminal depression," *J. of Pain & Symptom Management*, 1998, 16(3), 193-198.

Meyers, C.A., et al., "Methylphenidate therapy improves cognition, mood, and function of brain tumor patients," *J. of Clinical Oncology*, 1998, 16(7), 2522-2527.

Ohashi, N. et al., "Acyl(amino)naphthalene derivatives," CA 104:186157, 1985.

Olin, J. et al., "Psychostimulants for depression in hospitalized cancer patients," *Psychosomatics*, Jan.-Feb. 1996, 37(1), 57-62.

Patrick, K. et al., "Synthesis of deuterium labelled methylphenidate, p-Hydroxymethylphenidate, Ritalinic Acid and p-Hydroxyritalinic Acid," Journal of Labelled Compuinds and Radiopharmaceuticals, 1982, 9(4), 485-490.

Physician's Desk Reference, 46th Ed., 1992, 880-881.

Radloff, L.S., "The CES-D scale: a self-report depression scale for research in the general population," *Applied Psychological Measurement*, Summer 1977, 1(3), 385-401.

Rapport, M.D., et al., "Methylphenidate and desipramine in hospitalized children: I. Separate and combined effects on cognitive function," *J. of the Am. Acad. Of Chils Adolescent Psychiatry*, 1993, 32(2), 333-342.

Reitan, R.M., "Validity of the trail making test as an indicator of organic brain damage," *Perceptual Motor Skills*, 1958, 8, 271-276.

Roehrs, T., et al., "Sleepiness and the reinforcing and subjective effects of methylphenidate," *Exp. Clin, Psychopharmacol.*, 1999, 7(2), 145-150 (Abstract only).

Srinivas, N.R., et al., "In vitro hydrolysis of RR,SS0threo-methylphenidate by blood esterases-differential and enantioselective interspecies variability," *Chirality*, 1991, 3, 99-103.

Stiebel, V., et al., "Long-term methylphenidate use in the medically ill patient with organic mood syndrome," *Psychosomatics*, 1990, 31(4), 454-456.

Sun, Z. et al., "Methylphenidate is Steroselectively Hydrolzyed by Human carboxylesterase CES1A1," *The Journal of Pharmacology and Experimental Therapeutics*, 2004, 310(2), 469-476.

Tyndale, R.F., et al., "Neuronal cytochrome P45oIID1 (Debrisoquine/sparteine-type): potent inhibition of activity by(-)-cocaine and nucleotide sequence identity to human hepatic P450 gene CYP2D6," *Molecular Pharmacology*, 1991, 40(1), 63-68.

Vanderplas, B. et al., "A convenient synthesis of cis-1R-N-benzyl-2S-hydroxymethyl cyclohexylamine," CA 118:101538, 1992.

Weitzner M.A., et al., "Methylphenidate in the treatment of neurobehavioral slowing associated with cancer and cancer treatment," *J. Neuropsychiatry*, Summer 1995, 7(3), 347-350.

Wilens, T. E., et al., "Pharmacotherapy of attention-deficit/hyperactivity disprder," *Attention-Deficit Disorders with Comorbidities*, Ch. 16, 509-535 (1995).

Wilwerding, M. B. et al., "A randomized crossover evaluation of methylphenidate in cancer patients receiving strong narcotics," *Soc. Clin. Oncology*, 29th Annual Meeting, May 16-18, 1993, 1615, 1993, vol. 12, p. 464.

Yellen, S.B., et al., "Measuring fatigue and other anemia-related symptoms with the functional assesment of cancer therapy (FACT) measurement system," *J. pain Symptom Manage.*, Feb. 1997, 13(2), 63-74.

Complaint, filed Aug. 19, 2004, Civil Action No. 04-4030(SRC), *Celgene Corporation, Novartis Pharmaceuticals Corporation and Novartis Pharma AG v. teva Pharmaceuticals USA, Inc.*

Answer and Counterclaim of Defendant teva Pharmaceuticals USA, Inc., filed Noc. 9, 2004, Civil Action No. 04-4030(SRC), *Celgene Corporation, Novartis Pharmaceuticals Corporation and Novartis Pharma AG v. Teva Pharmaceuticals USA, Inc.*

Plaintiffs' Reply to Defendant's Counterclaim, filed Nov. 29, 2004, Civil Action No. 04-4030(SRC), *Celgene Corporation, Novartis Pharmaceuticals Corporation and Novartis Pharma AG v. Teva Pharmaceuticals USA, Inc.*

Redacted Amended Answer and Counterclaims of Defendant Teva Pharmaceuticals USA, Inc., filed Nov. 9, 2005, Civil Action No. 04-4030(SRC), *Celgene Corporation, Novartis Pharmaceuticals Corporation and Novartis Pharma AG v. Teva Pharmaceuticals USA, Inc.*

Plaintiffs' Reply to Defendant's Amended Counterclaims, filed Dec. 5, 2005, Civil Action No. 04-4030(SRC), *Celgene Corporation, Novartis Pharmaceuticals Corporation and Novartis Pharma AG v. Teva Pharmaceuticals USA, Inc.*

Beck, A.T., et al., "Assessment of depression: the depression inventory," *Mod. Probl. Pharmacopsychiatry*, 1974, 7, 155-169.

CAS RN6051-31-6 or RN 3019-58-7, May 22, 2001.

DeLong, R., et al., "Methylphenidate in neuropsychological Sequelae of radiotherapy and chemotherapy of childhood brain tumors and leukemia," *J. Child Neurology*, Oct. 1992, 7, 462-463.

Dobashi, A., et al., "Enantioselectivity of hydrogen-bond association in liquid-solid chromatography," *Journal of Liquid Chromatography*, 1986, 9(2 &3), 243-267.

*Japan Chem. Soc.*, "Organic reaction," 1958, 1(18), 504-505 (translated attached).

Licamele, W.L., et al., "The Concurrent use of lithium and methylphenidate in a child," *J. of the Am. Acad. Of Child Adolescent Psychiatry*, 1989, 28(5), 785-787.

Massie, M. J. et al., "Diagnosis and treatment of depression in the cancer patient," *Clinical Psychiatry*, Mar. 1984, vol. 45, 3(2), 25-29.

Morrison, R. T. et al., *Organic Chemistry*, 3rd Rd., Allyn & Bacon, Inc. 1973, 32-34.

Nakano, T. et al., Algorithm for the treatment of major depression in patients with advanced cancer, *Psychiatry and Clinical Neurosciences*, Proceedings of the International Meeting on Japanese Psychopharmacology Algorithms, Yokohama, Apr. 23, 1998, ISSN1323-1316, 1999, Supplement 53, S61-S65.

O'Neill, W. M., "The cognitive and psychomotor effects of opioid drugs in cancer pain management," *Cancer Surveys*, Palliative Medicine Problem Areas in Pain and Symptom Management, 1994, 21, 67-84.

Pelham, W. E. et al., "Sustained Release and Standard Methylphenidate Effects on Cognitive and Social Behavior in Children with Attention Deficit Disorder," *Pediatrics*, Oct. 1987, 80(4), 491-501.

Plutchik, L., et al., "Methylphenidate in post liver transplant patients," *Psychosomatics*, Mar. -Apr. 1998, 39(2), 119-123.

Reich, M.G., "Amphetamines in oncology: review of the literature," *Cancer*, 1996, 83, 891-900 (English abstract).

Soares, J.R., "Sterochemical studies on potential cantral nervous system active agents and studies on the chemistry of some 3-benzoylpiperidines," *UMI Dissertation Services*, 1971, 1-180.

Srinivas, N. R., Thesis entitled "Enantioselective Pharmacokintics of dl-threo-Methylphenidate in Children with Attention-Deficit Hyperactivity Disorder and Healthy Adults," Thesis submission date: Apr. 1991.

Teo, S. K., et al., "A single-dose, two-way crossover, bioequivalence study of dexmethylphenidate HCl with and without food in healthy subjects," *J. Clin, Pharmacol.*, Feb. 2004, 44, 173-178.

Thai, D.L., et al., "Comparative Pharmacokinetics and Tissue Distribution of the d-enantiomers of Para-substituted Methylphenidate Analogs," *Drug Metabolism and disposition*, 1999, 27(6), 645-650.

Vigano, A. et al., "Methylphenidate for the management of somatization in terminal cancer patients," *J Pain and Symptom Mangement*, Feb. 1995, 10(2), 167-170.

Weitzner, M. A. et al., "The functional assessment of cancer therapy (FACT) scale: development of a brain subscale and revalidation of the general version (FACT-G) in patients with primary brain tumors," *Cancer*, Mar. 1, 1995, 75(5), 1151-1161.

Yee, J. D. et al., "Dextroamphetamine of methylphenidate as adjuvants to opioid analgesia for adolescents with cancer," *J Pain and Symptom Management*, Feb. 1994, 9(2), 122-125.

In the United States District Court For The District of New Jersey, Civil Action No. 04-CV-04030 (FLW), (consolidated with Civil Action No. 06-6154 (FLW)), District of New Jersey; *Celgene Corporation, Novartis Pharmaceuticals Corporation and Novartis Pharma A.G. v. Teva Pharmaceuticals USA, Inc.*: Complaint for Patent Infringement with attached Exhibits A,B and C (Dec. 21, 2006).

In the United States District Court For The District of New Jersey, Civil Action No. 04/CV-04030 (FLW) and Civil Action No. 06-CV-6154 (FLW) , *Celgene Corporation, Novartis Pharmaceuticals Corporation and Novartis Pharma A.G. v. Teva Pharmaceuticals USA, Inc.*: First Amended Answer and Counterclaim of Defendant Teva Pharmaceuticals USA, Inc. in Civil Action No. 06-CV-6154 (FLW) (Mar. 23, 2007).

In the United States District Court For The District of New Jersey, Civil Action No. 04-cv-04030 (FLW) and Civil Action No. 06-CV-6154 (FLW) , *Celgene Corporation, Novartis Pharmaceuticals Corporation and Novartis Pharma A.G. v. Teva Pharmaceuticals USA, Inc.*: Plaintiff's Reply to Defendant's Fisrt Amended Counterclaim in Civil Action No. 06-CV-6154 (FLW) (Apr. 12, 2007).

In the United States District Court For The District of New Jersey, Civil Action No. 06-CV-05818 (SDW), *Celgene Corporation, Novartis Pharmaveuticals Corporation and Novartis Pharma A.G. v. Abrika Pharmaceuticals, Inc. and Abrika Pharmaceuticals, LLLP*: Complaint For Patent infringement with attached Exhibits A and B (Dec. 4, 2006).

In the United States District Court For The District of New Jersey, Civil Action No. 2:06-CV-05818 (SDW)(MCA), *Celgene Corporation, Novartis Pharmaceuticals Corporation and Novartis Pharma A.G. v. Abrika Pharmaceuticals, Inc. and Abrika Pharmaceuticals, LLLP* Answer and Counterclaim (Jun. 1, 2007).

In the United States District Court For The District of New Jersey, Civil Action No. 06-CV-05818 (SDW), *Celgene Corporation,*

*Novartis Pharmaceuticals Corporation and Novartis Pharma A.G.* v. *Abrika Pharmaceuticals, Inc. and Abrinks Pharmaceuticals, LLLP*: Plaintiff's Reply to the Counterclaim (Jun. 25, 2007).

In the United States District Court For The District of New Jersey, Civil Action No. 07-CV-04459 (FLW)(JJH), *Celgene Corporation, Novartis Pharmaceuticals Corporation and Novartis Pharma A.G.* v. *Teva Pharmaceuticals USA, Inc.*: Complaint for Patent Infringement with attached Exhibits A-E (Sep. 14, 2007).

In the United States District Court For The District of New Jersey, Civil Action No. 2:06-CV-05818, *Celgene Corporation, Novartis Pharmaceuticals Corporation and Novartis Pharma A.G.* v. *Abrika Pharmaceuticals, Inc. and Abrika Pharmaceuticals, LLLP*: Dfendant's First Supplemental Response to Plaintiff Celgene Corporation's Interrogatories Nos. 6-10 (Sep. 28, 2007).

In the United States District Court For The District of New Jersey, Civil Action No. 2:07-cv-04819-SDW-MCA, *Celgene Corporation, Novartis Pharmaceuticals Corporation and Novartis Pharma A.G.* v. *KV Pharmaceutical Company*: Complaint for Patent Infringement with attached Exhibits A and B (Oct. 4, 2007).

In the United States District Court For The District of New Jersey, Civil Action No. 3:07-cv-04854-FLW-JJH, *Celgene Corporation, Novartis Pharmaceuticals Corporation and Novartis Pharma A.G.* v. *Intellipharmaceutics Corp.*: Complaint For patent Infringement with attached Exhibits A-E (Oct. 5, 2007).

In the United States District Court For The District of New Jersey, *Celgene Corporation, Novartis Pharmaceuticals Corporation and Novartis Pharma A.G.* v. *Barr Laboratories, Inc. and Barr Pharmaceuticals, Inc.*: Complaint For Patent Infringement with attached Exhibits A & B (Oct. 3, 2007).

In the United States District Court For The District of New Jersey, Civil Action No. 04-CV-4030 (SRC), *Celgene Corporation, Novartis Pharmaceuticals Corporation and Novartis Pharma A.G.* v. *Teva Pharmaceuticals USA, Inc.*: Defendant Teva Pharmaceuticals USA, Inc.'s Supplemental Responses to Plaintiff Celgene Corporation's First Set of Interrogatory Nos. 1-2, 4-7 and 10-15 (Jul. 14, 2005.

In the United States District Court For The District of New Jersey, Civil Action No. 04-CV-4030 (SRC), *Celgene Corporation, Novartis Pharmaceuticals Corporation and Novartis Pharma A.G.* v. *Teva Pharmaceuticals USA, Inc.*: Defendant Teva Pharmacceuticals USA, Inc.'s Second Supplemental Responses to Plaintill Celgene Corporation's First Set of Interrogatory Nos. 1, 5, 10-11, and 14.

Confidential, Trade Secret, and/or Proprietary Document, dated Jul. 8, 2004.

Confidential, Trade Secret, and/or Proprietary Document, dated Jul. 27, 2004.

Confidential, Trade Secret, and/or Proprietary Document, dated Oct. 23, 2006.

Confidential, Trade Secret, and/or Proprietary Document, dated Aug. 3, 2007.

Confidential, Trade Secret, and/or Proprietary Document, dated Aug. 21, 2007.

Confidential, Trade Secret, and/or Proprietary Document, dated Aug. 23, 2007.

Confidential, Trade Secret, and/or Proprietary Document, dated Sep. 17, 2007.

Confidential, Trade Secret, and/or Proprietary Document, dated Sep. 26, 2007.

Confidential, Trade Secret, and/or Proprietary Document, dated Oct. 5, 2007.

In the United States District Court For The District of New Jersey, Civil Action No. 07-CV-4459 (FLW), *Celgene Corporation, Novartis Pharmaceuticals Corporation and Novartis Pharma A.G.* v. *Teva Pharmaceuticals USA, Inc.*: Teva's Answer and Counterclaims, Nov. 5, 2007.

In the United States District Court For The District of New Jersey, Civil Action No. 07-CV-4459 (FLW), *Celgene Corporation, Novartis Pharmaceuticals Corporation and Novartis Pharma A.G.* v. *Teva Pharmaceuticals USA, Inc.*: Plaintiffs' Reply to Defendant's Counterclaims, Nov. 28, 2007.

In the United States District Court For The District of New Jersey, Civil Action No. 07-CV-4854 (FLW) (JJH), *Celgene Corporation, Novartis Pharmaceuticals Corporation and Novartis Pharma A.G.* v. *Intellipharmaceuticals Corp.*: Answer and Counterclaims Demand For Jury Trial, Nov. 20, 2007.

In the United States District Court For The District of New Jersey, Civil Action No. 07-CV-4854 (FLW) (JJH), *Celgene Corporation, Novartis Pharmaceuticals Corporation and Novartis Pharma A.G.* v. *Intellipharmaceuticals Corp.*: Plaintiffs' Reply to Defendants's Counterclaims, Dec. 28, 2007.

In the United States District Court For The District of New Jersey, Civil Action No. 07-CV-5367 (FLW) (TJB), *Celgene Corporation, Novartis Pharmaceuticals Corporation and Novartis Pharma A.G.* v. *Actavis South Atlantic LLC and Abrika Pharmaceuticals, Inc.*: Complaint for Patent Infringement, Nov. 8, 2007.

In the United States District Court For The District of New Jersey, Civil Action No. 07-CV-5367 (FLW) (TJB), *Celgene Corporation, Novartis Pharmaceuticals Corporation and Novartis Pharma A.G.* v. *Actavis South atlantic LLC and Abrika Pharmaceuticals, Inc.*: Answer and Counterclaims, Dec. 18, 2007.

In the United States District Court For The District of New Jersey, Civil Action No. 07-CV-5367, *Celgene Corporation, Novartis Pharmaceuticals Corporation and Novartis Pharma A.G.* v. *Actavis South Atlantic LLC Abrika Pharmaceuticals, Inc.*: Plaintiffs' Resply to Defendants' Answer and Counterclaims, Jan. 25, 2008.

In the United States District Court For The District of New Jersey, Civil Action No. 07-CV-5552 (SDW) (MCA), *Celgene Corporation, Novartis Pharmaceuticals Corporation and Novartis Pharma A.G.* v. *Barr Pharmaceuticals, Inc. and Barr Laboratories, Inc.*: Complaint for Patent Infringement, Nov. 16, 2007.

In the United States District Court For The District of New Jersey, Civil Action No. 07-CV-5552 (SDW) (MCA), *Celgene Corporation, Novartis Pharmaceuticals Corporation and Novartis Pharma A.G.* v. *Barr Pharmaceuticals, Inc. and Barr Laboratories, Inc.*: Defendants' Answer, Affirmative Defenses, Counterclaims and Jury Demand, Jan. 25, 2008.

In the United States District Court For The District of New Jersey, Civil Action No. 07-CV-5552 (SDW) (MCA), *Celgene Corporation, Novartis Pharmaceuticals Corporation and Novartis Pharma A.G.* v. *Barr Pharmaceuticals, Inc. and Barr Laboratories, Inc.*: Plaintiffs' Reply to Defendants' Counterclaims, Mar. 5, 2008.

In the United States Patent and Trademark Office, File History of Ex Parte Reexamination of Patent No. 6,355,656, Control. No. 90/007,177, Reexamination Certificate Issued on Mar. 27, 2007.

\* cited by examiner

DELIVERY OF MULTIPLE DOSES OF MEDICATIONS

CROSS-REFERENCE TO RELATED APPLICATIONS

This application is a continuation application of application Ser. No. 09/038,470, filed Mar. 11, 1998, now U.S. Pat. No. 6,635,284, which is a divisional application of application Ser. No. 09/892,190, filed Jul. 14, 1997, now U.S. Pat. No. 5,837,284, which is a continuation-in-part of application Ser. No. 08/647,642, filed May 15, 1996, now abandoned, and a continuation-in-part of application Ser. No. 08/583,317, filed Jan. 5, 1996, now U.S. Pat. No. 5,733,756, and application Ser. No. 08/567,131, filed Dec. 4, 1995, now abandoned, all of which are incorporated herein by reference.

FIELD OF THE INVENTION

The present invention relates to improved dosing of medications. In particular, the present invention relates to improved dosing of a medication whereby two or more effective, time-separated doses may be provided by administration of a single dosage unit. The second, and any later, dose is time-delayed following administration. Based on predictable in vitro release times, the dosage forms can be formulated to deliver delayed doses in vivo at desired times.

The dosage forms and methods of the present invention are particularly suitable for the administration of methylphenidate hydrochloride, and especially for the administration of a single isomer, d-threo-methylphenidate hydrochloride.

The administration of dosage forms which contain an immediate dosage and a delayed second dosage provides for reduced abuse potential, improved convenience of administration, and better patient compliance, especially when methylphenidate is used to treat certain central nervous system disorders.

BACKGROUND OF THE INVENTION

Attention Deficit Disorder (ADD), a commonly diagnosed nervous system illness in children, is generally treated with methylphenidate hydrochloride (available commercially as, e.g., Ritalin®). Symptoms of ADD include distractibility and impulsivity. A related disorder, termed Attention Deficit Hyperactivity Disorder (ADHD), is further characterized by symptoms of hyperactivity, and is also treated with methylphenidate hydrochloride. Methylphenidate drugs have also been used to treat cognitive decline in patients with Acquired Immunodeficiency Syndrome (AIDS) or AIDS related conditions. See, e.g., Brown, G., *Intl. J. Psych. Med.* 25(1): 21–37 (1995); Holmes et al., *J. Clin. Psychiatry* 50: 5–8 (1989).

Methylphenidate exists as four separate optical isomers as follows:

l-threo d-erythro d-threo l-erythro wherein $R_2$ is phenyl. Pharmaceutically acceptable salts are generally administered clinically. Other phenidate drugs, which also can be administered according to the invention, include those in which the methyl group in the above structures is replaced by $C_2$–$C_4$ alkyl and $R_2$ is optionally substituted with $C_1$–$C_4$ alkyl.

Clinically, the threo pair of enantiomers of methylphenidate hydrochloride is generally administered for the treatment of ADD and ADHD. The hydrochloride salt is commonly referred to simply as "methylphenidate". Unless indicated otherwise, the term "methylphenidate" is used broadly herein to include methylphenidate and pharmaceutically acceptable salts thereof, including methylphenidate hydrochloride.

The threo racemate (pair of enantiomers) of methylphenidate is a mild central nervous system stimulant with pharmacological activity qualitatively similar to that of amphetamines. Undesirable side effects associated with the use of the dl-threo racemate of methylphenidate include anorexia, weight loss, insomnia, dizziness and dysphoria. Furthermore, the racemate, which is a Schedule II controlled substance, produces a euphoric effect when administered intravenously or through inhalation or ingestion, and thus carries a high potential for abuse.

Srinivas et al. studied the administration of dl-threo-, d-threo, and l-threo-methylphenidate to children suffering from ADHD, and reported that the pharmacodynamic activity of dl-threo-methylphenidate resides in the d-threo isomer (*Clin. Pharmacol. Ther.*, 52: 561–568 (1992)). Therefore, while dl-threo-methylphenidate is generally used therapeutically, this racemate includes the l isomer which apparently makes no significant contribution to the pharmacological effectiveness of the drug, but likely contributes to the associated side effects. It is thus desirable to administer only the active d-threo form of the drug.

An additional problem is that children being treated with dl-threo methylphenidate must generally take one or more doses during the day. This creates a problem for school administrators who must store a controlled substance on school premises, with the associated risk that it may be stolen for illicit use. Furthermore, children may be traumatized by ridicule from peers when they must take medication at school.

Sustained release formulations of dl-threo methylphenidate have been developed, which provide for slow release of the drug over the course of the day. However, it has been observed that peak plasma concentrations of the drug are lower when sustained release formulations are used. In some studies, sustained release formulations of methylphenidate have been shown to have lower efficacy than conventional dosage forms.

There remains a need for methods for delivering methylphenidate with maximum effectiveness and minimal potential for abuse. Furthermore, it has been determined that there is a need for a dosage form which provides, in one administration, an initial release followed, at a predictable delay, by a second release, of maximally effective methylphenidate. This will eliminate the risk of theft or loss of the second dose, while minimizing undesirable side effects and maximizing ease of administration. The present invention is directed to these, as well as other, important ends.

SUMMARY OF THE INVENTION

The present invention provides, in one embodiment, a therapeutic composition for the oral administration of a methylphenidate drug comprising a dosage form containing two groups of particles, each containing the methylphenidate drug. The term "particles", as used herein, includes pellets, granules, and the like. The first group of particles provides a substantially immediate dose of the methylphenidate drug upon ingestion by a mammal. The first group of particles can also comprise a coating and/or sealant. The second group of particles comprises coated particles, which comprise from about 2% to about 75%, preferably from about 2.5% to about 50%, and more preferably from about 5% to about 20%, by weight of the second group of particles, of the methylphenidate drug, in admixture with one or more binders. The coating comprises a pharmaceutically acceptable ammonio methacrylate copolymer in an amount sufficient to provide a delay of from about 2 hours to about 7 hours following ingestion before release of the second dose. If desired, one or more additional doses may be delivered by additional particles, coated in a similar manner, but with a sufficient amount of ammonio methacrylate copolymer coating to provide the dosage after an additional delay. Methylphenidate and pharmaceutically acceptable salts thereof, including methylphenidate hydrochloride, can be prepared into the dosage forms of the invention.

In one embodiment of the present invention, the first group of particles comprises a methylphenidate drug and provides a substantially immediate dose of the methylphenidate drug upon ingestion by a mammal. The first group of particles may comprise a coating and/or sealant. The second group of particles comprises coated particles, which comprise from about 2% to about 75%, preferably from about 2.5% to about 50%, and more preferably from about 5% to about 20%, by weight of the particles of the methylphenidate drug in admixture with one or more binders. The coating comprises a pharmaceutically acceptable ammonio methacrylate copolymer in a quantity sufficient to provide a dose of methylphenidate delayed by from about 2 hours to about 7 hours following ingestion.

For example, the first group of particles can comprise a pharmaceutically acceptable salt of methylphenidate, such as methylphenidate hydrochloride, in powder form, or coated or uncoated particles containing the methylphenidate salt. The amount of methylphenidate salt in each group of particles can vary, depending upon the dosage requirements of the patient to whom the drug is to be administered. Generally, the daily dosage requirement for methylphenidate drugs is from about 1 mg to about 50 mg per day, preferably from about 2 mg to about 20 mg, and more preferably from about 2.5 to about 12 mg per day. The actual dosage to be administered will be determined by the attending physician as a matter of routine. Thus, depending upon the amounts of coating and/or and optional excipients and other additives, the amount of methylphenidate drug can be, for example, from about 2% to about 99% by weight of the first group of particles. In addition to the methylphenidate drug, the second group of particles comprises a filler, such as a hydrophobic filler, one or more ammonio methacrylate copolymers, and optional excipients and other additives. The filler can be present in an amount of, for example, from about 35% to about 45%, by weight, based on the total weight of the second group of particles.

Another embodiment of the present invention provides a method for treating disease, such as, for example, ADD, ADHD, or AIDS-related dementia, in a patient in need of treatment. This treatment comprises administering to the patient a dosage form providing once-daily oral administration of a methylphenidate drug such as methylphenidate hydrochloride. The dosage form comprises at least two groups of particles, each containing the methylphenidate drug. The first group of particles comprises from about 2% to about 99% by weight of the methylphenidate drug, depending upon desired the daily dosage, and provides a substantially immediate dose of methylphenidate upon ingestion by a mammal. The first group may comprise a coating and/or sealant. The second group of particles comprises coated particles. The coated particles comprise the methylphenidate drug in admixture with one or more binders, wherein the amount of methylphenidate drug is from about 2% to about 75%, preferably from about 2.5% to about 50%, and more preferably from about 5% to about 20%, by weight of the second group of particles, and a coating comprising an ammonio methacrylate copolymer in a quantity sufficient to provide a dose of methylphenidate delayed by from about 2 hours to about 7 hours following ingestion. The components of the two groups of particles can vary as described hereinabove. The initial dose can be administered separately from the delayed dose, if desired.

A further embodiment of the present invention provides dosage forms for the oral administration, in a single dosage form, of two doses of a pharmaceutically acceptable salt of d-threo-methylphenidate. The dosage forms comprise particles containing within their interiors from about 2% to about 75%, preferably from about 2.5% to about 50%, and more preferably from about 5% to about 20%, of the d-threo-methylphenidate salt, in admixture with one or more binders. The particles have a coating exterior to the methylphenidate salt, which comprises an ammonio methacrylate copolymer in a quantity sufficient to delay release of the d-threo-methylphenidate salt contained within by from about 2 hours to about 7 hours following administration. The dosage forms also comprise, exterior to the coating, an outer layer comprising from about 2% to about 99% by weight of the d-threo-methylphenidate salt, based on the weight of all components in the outer layer, to provide a substantially immediate dose of the d-threo-methylphenidate salt upon administration. The layer comprising the immediate dose of the d-threo-methylphenidate salt can, if desired, further comprise an outer sealant layer. If desired, the two doses of the d-threo-methylphenidate salt can be approximately equal.

The present invention also provides dosage forms providing plasma concentration profiles for methylphenidate having two maxima, temporally separated from each other by from about 2 hours to about 7 hours. Preferably, the magnitude of said maxima differs by no more than about 30 percent, more preferably by no more than about 20 percent, and most preferably by no more than about 10 percent.

"Methylphenidate" as used herein, includes all four optical isomers of the compound and all pharmaceutically acceptable salts thereof. When one or more particular isomers is contemplated, the isomer is indicated, as in d-threo, l-threo, etc. The combined threo isomers may be indicated simply as "threo" and the erythro isomers as "erythro". For therapeutic use in treating conditions treatable by methylphenidate drugs, dl-threo methylphenidate hydrochloride is generally used, while d-threo methylphenidate hydrochloride is preferred according to the present invention.

As discussed, the four isomers have exhibited varying levels of therapeutic activity, and have been shown to differ generally in producing unwanted side effects. The present invention provides dosage forms which maximize therapeutic effectiveness and minimize undesirable side effects. In certain preferred embodiments, the dosage forms of the present invention provide administration of the two threo forms of methylphenidate. In particularly preferred embodiments, the dosage forms of the present invention provide administration of a single isomer, d-threo-methylphenidate, albeit in two or more doses.

The dosage forms of the present invention are intended for oral ingestion by a mammal, particularly a human. The dosage forms of the present invention are particularly suitable for the administration of methylphenidate drugs, in at least two doses. Most preferably, the dosage forms provide two doses of a d-threo methylphenidate drug such as d-threo methylphenidate hydrochloride. The second dose can be delayed by from about 2 hours to about 7 hours, preferably from about 3 hours to about 6 hours, and most preferably from about 4 hours to about 5 hours, following ingestion of the dosage form by a mammal. This eliminates the need for a patient, for example a child being treated for ADD, to carry a second dose for ingestion several hours after ingestion of a first dose. The exclusion of the l isomers and the d-erythro isomer eliminates the concurrent ingestion of forms of methylphenidate principally believed to be associated with adverse side effects and/or reduced effectiveness.

Figure 1:
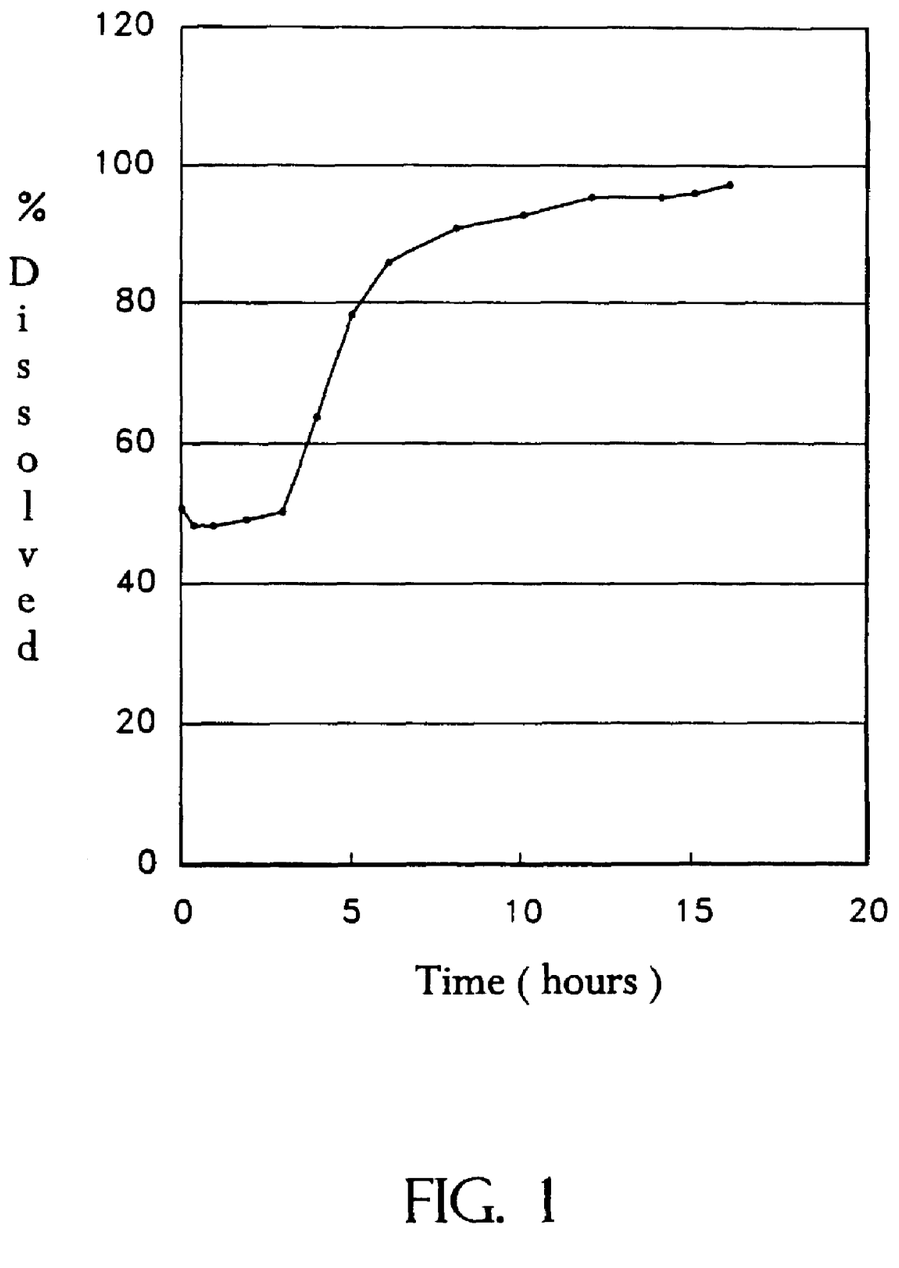
FIG. 1 depicts an in vitro time-concentration relationship (release profile) for certain preferred dosage forms in accordance with the invention.

The temporal separation of the two doses provided according to the present invention can be represented graphically as in FIG. 1. FIG. 1 is an in vitro drug release profile of a dosage form of the present invention. The data were obtained by measuring the rate of dissolution of drug as a function of time. In this embodiment two doses are provided. The release of the first dose preferably occurs substantially immediately; for example, within about 30 minutes following administration. Following a period of little or substantially no drug release, the second dose is released. The two releases can be referred to as "pulses", and such a release profile can be referred to as "pulsatile".

Figure 2:
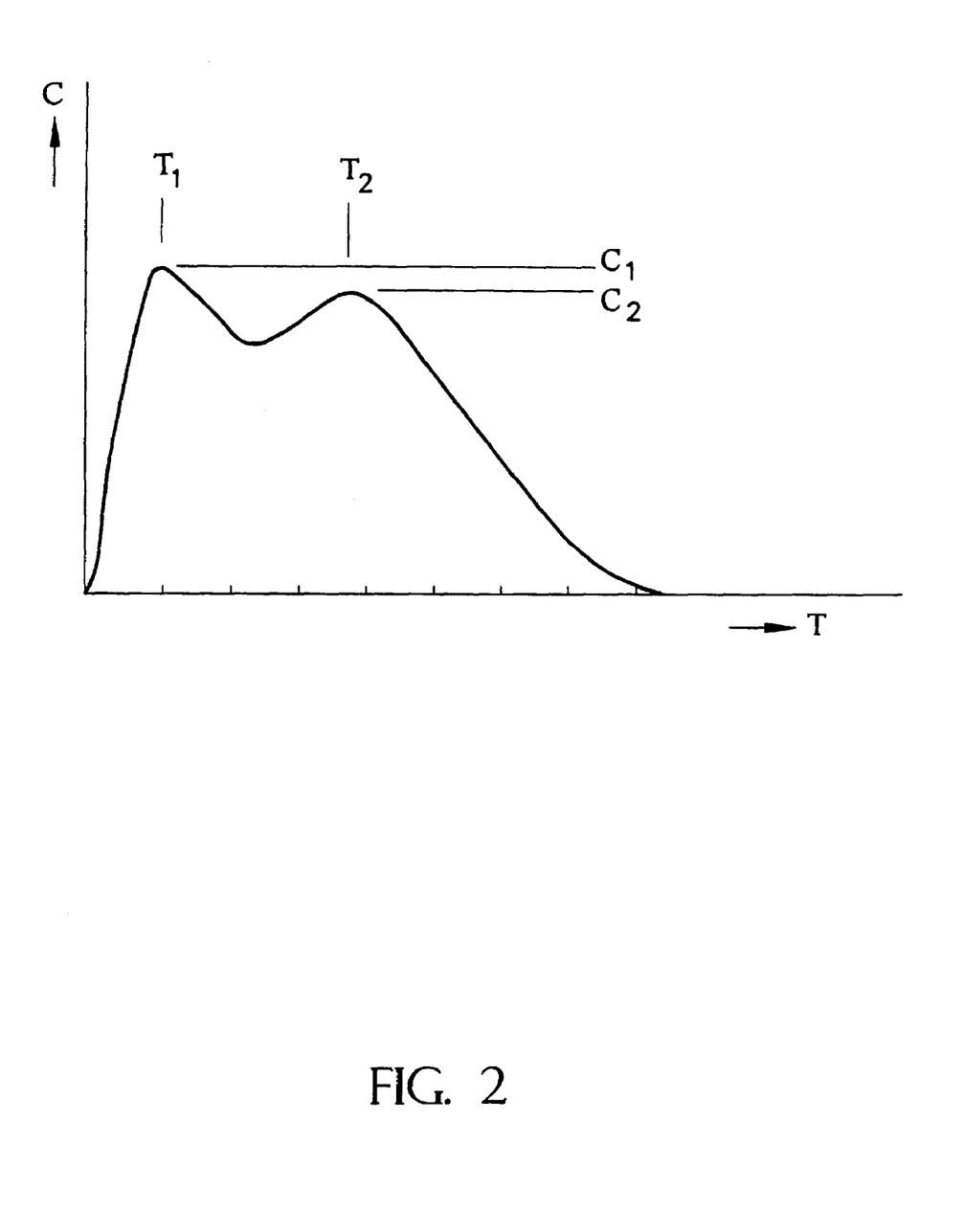
FIG. 2 depicts a schematic representation of in vivo plasma concentration of a drug released according to the release profile shown in FIG. 1.

FIG. 2 is a schematic representation of the plasma concentration of drug resulting from a release profile according to FIG. 1. The maximum concentration due to the first dose, $C_1$, occurs at $t_1$, preferably from about 1 hour to about 3 hours after ingestion, most preferably about 2 hours after ingestion. The release of the first dose is followed by a period during which substantially no drug is released, which lasts approximately 2–6 hours, preferably 3–5 hours, post ingestion. The second dose is then released, with the maximum concentration, $C_2$, at $t_2$, which is preferably about 6 hours post-ingestion. Preferably at least about 80% of the total drug has been released by about 6 hours following administration. In the embodiment represented by FIG. 2, the levels of drug released at the two maxima are nearly equal. Preferably, if two approximately equal doses are released, the release of the two doses provides a plasma concentration profile having two maxima, which differ from each other by no more than about 40 percent in magnitude, preferably by no more than about 30 percent, and more preferably by no more than about 25 percent. This is determined by the relationship:

$$|C_1 - C_2|/C_1$$

In such embodiments is most preferred that the maxima differ by no more than 20%. However, embodiments in which the maxima of the two releases differ by more than 40 percent are within the scope of the invention. The appropriate relative amounts of drug in each release can be readily determined by one skilled in the art.

Dosage forms of the present invention provide controlled release of a methylphenidate drug, including pharmaceutically acceptable salts of methylphenidate, whereby an initial dose for immediate release can be combined with a delayed release of one or more additional doses. Such dosage forms may alternatively be referred to as "pulsatile" dosage forms.

"Immediate release", as used herein, means release within about a half hour following ingestion, preferably about 15 minutes, and more preferably within about 5 minutes following ingestion. "Delayed release", as used herein, refers to a drug release profile which includes a period during which no more than about 10 percent of the drug in a particular dosage form is released, followed by a period of from about 0.5 hour to about 2.5 hours, preferably about 1.5 hours, more preferably about 1 hour, in which no less than about 70 percent, preferably no less than about 80 percent, and more preferably no less than about 90 percent, of the drug is released. The terms "medication" and "drug" are used interchangeably herein.

According to the present invention, delayed release dosage forms can be combined with forms which provide immediate release of a drug. Thus, two or more dosage forms can be combined, one dosage form providing a portion of a patient's daily dosage needs of a drug and subsequent dosage forms providing additional portions of a patient's daily dosage needs. For example, a drug can be administered to a patient in two dosage forms simultaneously, one providing, e.g., about 30–50 percent of the patient's daily requirement of the drug and the second providing the remainder of the patient's daily requirement. Alternatively, and preferably, a single dosage form can be administered which includes an immediate dose of some portion of a patient's daily requirement and one or more delayed doses to provide the remaining portion or portions of the patient's daily requirement.

Dosage forms of the present invention provide an initial dose of a drug such as, for example, a pharmaceutically acceptable salt of d-threo-methylphenidate (also referred to herein as d-MPD), followed by an interval wherein substantially no additional drug is released, followed in turn by release of a second dose. If desired, a second substantially release-free interval may be provided following the second release, followed in turn by a third dose. Thus, dosage forms providing 3 or more doses are contemplated by the present invention. However, dosage forms providing 2 or 3 doses are generally preferred for therapeutic use, with 2 doses being more preferred. For example, the first dose can provide from about 30 percent to about 70 percent of a patient's daily prescribed intake of the drug and the second dose provides from about 70 percent to about 30 percent. If two approximately equal doses are desired, the initial dose preferably provides from about 40 percent to about 60 percent, and the second dose preferably provides from about 60 percent to about 40 percent, of a patient's prescribed daily intake of the drug. If desired, the first dose and the second dose can each provide about 50 percent of a patient's prescribed daily intake of drug. However, as will be apparent to one skilled in the art, the effect of drug metabolism in the body may require adjustment of the relative amounts of each dose, so that, for example, the second dose may have to be adjusted to provide more of the drug than the first dose, to compensate for any competition between drug release and drug metabolism. This can be observed in FIG. 2, which, as discussed above, represents the blood plasma level of a drug, such as a methylphenidate drug, delivered in a dosage form which provides a release profile as illustrated in FIG. 1.

The initial dose of methylphenidate drug in the dosage forms of the present invention can be provided by incorporating the methylphenidate drug into a form which allows for substantially immediate release of the drug once the dosage form is ingested by a patient. Such forms include, for example, powders, coated and uncoated pellets, and coated and uncoated tablets. The dose for immediate release can be administered in a tablet or capsule form which may also include the delayed dose. For example, two or more groups of pellets may be combined within a hard gelatin capsule or compressed into a tablet. Powders can be granulated and can be combined with pellets and excipients and/or other additives, and contained within a capsule or compressed into a tablet. These and other dosage forms will be familiar to those skilled in the art.

The delayed dose of a methylphenidate drug in the dosage forms of the present invention is provided in part by the use of certain copolymers referred to as "ammonio methacrylate copolymers". Ammonio methacrylate copolymers comprise acrylic and/or methacrylic ester groups together with quaternary ammonium groups. According to the present invention, the copolymers are incorporated into a formulation which is used to coat particles containing a medication.

The "acrylic and/or methacrylic ester groups" in the copolymers used in the compositions and methods of the present invention are referred to herein collectively as "acrylic groups". The acrylic groups are preferably derived from monomers selected from $C_1$–$C_6$ alkyl esters of acrylic acid and $C_1$–$C_6$ alkyl esters of methacrylic acid. Preferred are $C_1$–$C_4$ alkyl esters of acrylic acid and methacrylic acid. Suitable monomers include, for example, methyl acrylate, ethyl acrylate, methyl methacrylate, and ethyl methacrylate. Ethyl acrylate and methyl methacrylate are preferred, and copolymers containing ethyl acrylate and methyl methacrylate are highly preferred. Also preferably, the copolymers have a molecular weight of about 150,000.

Quaternary ammonium groups in copolymers useful in forming coatings for use in the dosage forms of the present invention can be derived from monomers comprising quaternary ammonium groups. Preferably, the monomers are alkyl esters of acrylic or methacrylic acid, comprising alkyl groups having from 1 to 6 carbon atoms and a quaternary ammonium group in the alkyl portion. Monomers comprising quaternary ammonium groups can be prepared, for example, by reaction of monomers containing amino groups with alkylating agents such as, for example, alkyl halides, especially methyl chloride. Suitable monomers containing amino groups include 2-(N,N-dibutylamino) ethyl acrylate, 2-(N,N-dibutylamino) ethyl methacrylate, 4-diethylamino-1-methyl-butyl acrylamide, and 4-diethylamino-1-methyl-butyl methacrylamide. Other useful monomers containing amino groups are disclosed in U.S. Pat. No. 5,422,121, the disclosure of which is incorporated herein by reference. Particularly preferred as a monomer comprising a quaternary ammonium group is trimethylammonioethyl methacrylate chloride (TAMCl).

While ammonio methacrylate copolymers such as those described herein have been used for sustained delivery of certain medicaments, i.e., for the relatively constant administration of a drug, it has been surprisingly and unexpectedly found that dosage forms comprising a methylphenidate drug and a coating prepared from one or more ammonio methacrylate copolymers and certain fillers, can provide delayed or pulsatile release of the drug, a very distinct phenomenon. Methylphenidate drugs are amine-containing, rely upon body or membrane loading for efficacy, and are psychotropic. The ability to provide delayed release of a methylphenidate drugs using ammonio methacrylate copolymers is due to a combination of factors, including the composition of the ammonio methacrylate copolymers used, and the amount and composition of filler.

The ratio of acrylic groups to quaternary ammonium groups in the ammonio methacrylate copolymers influences the properties of the copolymers utilized in forming the coatings of the present invention. For use in the dosage forms and methods of the present invention, the ratio of acrylic groups to quaternary ammonium groups in the copolymers is preferably from about 10:1 to about 50:1, more preferably from about 15:1 to about 45:1. Preferably, in preparing a dosage form according to the present invention, two or more copolymers are used in combination. Also preferably, one of the copolymers comprises acrylic groups and quaternary ammonium groups in a ratio of from about 25:1 to about 45:1, more preferably from about 30:1 to about 40:1, and another of the copolymers comprises acrylic groups and quaternary ammonium groups in a ratio of from about 10:1 to about 25:1, more preferably from about 15:1 to about 20:1. Even more preferably, two ammonio methacrylate copolymers are used: a first copolymer comprising acrylic groups and quaternary ammonium groups in a ratio of from about 30:1 to about 40:1 and the second copolymer comprising acrylic groups and quaternary ammonium groups in a ratio of from about 15:1 to about 20:1. Most preferably, the copolymers are copolymers of methyl methacrylate, ethyl acrylate, and TAMCl, in ratios of 2:1:0.1 for the first copolymer and 2:1:0.2 for the second copolymer.

When two such ammonio methacrylate copolymers are used to form the coatings, the relative amounts of the two polymers is partly determinative of the delay and release properties of the dosage forms of the present invention. It is preferred that the ratio between the first polymer, most preferably having an acrylic group/quaternary ammonium group ratio of from about 30:1 to about 40:1, and the second polymer, most preferably having an acrylic group/quaternary ammonium group ratio of from about 15:1 to about 20:1, be from about 93:7 to about 97:3. More preferably, the ratio of the first polymer to the second polymer is from about 96:4 to about 94:6, and most preferably about 95:5.

Ammonio methacrylate copolymers used in the coatings of the dosage forms of the present invention can be prepared by methods known to those skilled in the art. Exemplary methods include emulsion polymerization, bulk polymerization and suspension polymerization. A suitable procedure is described in U.S. Pat. No. 3,979,349, the disclosure of which is incorporated herein by reference. Suitable ammonio methacrylate copolymers are known per se, and can be purchased from commercial providers. For example, suitable ammonio methacrylate polymers are available from Hüls America under the Eudragit® trademarks. The Eudragit® polymers and similar polymers, including methods for preparation, are described in Klaus O. R. Lehman, "Chemistry and Application Properties of Polymethacrylate Coating Systems", *Aqueous Polymeric Coatings for Pharmaceutical Dosage Forms*, 2nd. Ed., pp. 101–174, James Mc Ginity, Ed., Marcel Dekker, Inc., NY (1996), the disclosure of which is incorporated herein by reference.

The coatings of the present invention also preferably include a filler. The filler is preferably in powder form and is preferably hydrophobic. Exemplary fillers include talc, colloidal silica, fumed silica, gypsum, and glycerine monostearate. Talc is a particularly preferred filler.

The quantity of filler used in preparing coatings for the dosage forms of the present invention should be sufficient to minimize agglomeration of the particles. Agglomeration is highly undesirable because the agglomerates, rather than discrete particles, will become coated. Agglomerates are susceptible to breaking into discrete particles, which will be partially uncoated, resulting in unwanted variability in release rates. Preferably, the amount of filler is from about 30 percent to about 50 percent by weight, based on the total weight of the dry polymer, commonly referred to as "total solids". More preferably the amount of filler is from about 35 percent to about 45 percent of total solids, and most preferably about 40 percent.

Coatings used in the dosage forms of the present invention also preferably include a material which improves the processing of the copolymers. Such materials are generally referred to as "plasticizers" and include, for example, citric acid esters, adipates, azelates, benzoates, citrates, stearates, isoebucates, sebacates, propanetriol acetate, polyethylene glycols, diethyl phthalate, dibutyl sebacate, propylene glycol and ethylene glycol. Citric acid esters are preferred, and triethyl citrate is particularly preferred. The amount of plasticizer to be used in the coating is preferably from about 10 percent to about 30 percent, more preferably from about 15 percent to about 25 percent, and most preferably about 20 percent, based on the weight of the dry polymer, i.e., total solids.

Dosage forms of the present invention preferably comprise particles containing d-MPD. In one embodiment, the dosage form comprises two groups of particles. A first group of particles provides the initial dose of d-MPD. As stated hereinabove, the initial dose can be in powder, pellet or other particulate form and can be uncoated. If the initial dose is in the form of a powder or sufficiently small particles, it can, if desired, be pressed into a solid form such as a tablet or caplet. In this embodiment, the delayed dose is provided by a second group of particles. The second group of particles is preferably in the form of pellets. The pellets can be of any shape, such as, for example, spheroids or ellipsoids, or may be irregularly shaped.

Suitable pellets for the initial dose and/or the second dose can be formed by, for example, depositing a layer of drug, and optional excipients, carriers, and other optional materials, onto small, pharmaceutically acceptable particles such as nonpareils. Such a layer can be deposited by methods known to those skilled in the art, such as, for example, spraying, using methods and equipment known to those skilled in the art. For example, a Wurster air suspension coater can be used. Spraying can also be accomplished using a pan coating system, wherein the drug is deposited by successive spraying accompanied by tumbling in a rotating pan. Alternatively, pellets can be formed, for either or both of the initial and delayed dose, by extrusion of the drug with suitable plasticizers and other processing aids as necessary.

Tablets or caplets, or other solid dose forms, comprising the initial dose and/or delayed dose or doses, can conveniently be administered. A solid dose form can be prepared by methods known to those skilled in the art. For example, the d-MPD, filler and other optional components may be compressed into tablets or inserted into capsules. If desired, the drug and other components of the dose form can be granulated, using processing aids, fillers, aqueous or non-aqueous solvents, and binders known to those skilled in the art. Granules can be filled into capsules, if desired. Alternatively, the d-MPD can be blended with a solvent and processed by known methods such as ball-milling, calendering, stirring, or roll-milling, then pressed into a desired shape. Suitable solvents useful in forming the particles comprising d-MPD, and other components of the dosage forms of the invention, include inert organic and inorganic solvents which do not adversely affect the components of the dosage forms. While water can be used for many drugs, including methylphenidate, useful solvents can be selected from the group consisting of aqueous solvents, alcohols, ketones, esters, ethers, aliphatic hydrocarbons, halogenated solvents, cycloaliphatics, aromatic heterocyclic solvents, and mixtures thereof. Other solvents include acetone, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, nitroethane, nitropropane, tetrachloroethane, diglyme, and aqueous and non-aqueous mixtures thereof, such as acetone and water, acetone and methanol, acetone and ethyl alcohol, and ethylene dichloride and methanol.

Following the formation of suitable particles, those particles to be used to deliver the delayed dose are then coated with a polymer-containing coating as described herein. The amount of coating to be used in forming the dosage forms, particularly the delayed dose, of the present invention, will be determined by the desired delivery properties, including the amount of drug to be delivered, the delay time required, and the size of the particles. Preferably, the coating on the particles providing the delayed dose, including all solid components of the coating such as copolymer, filler, plasticizer and optional additives and processing aids, is from about 10 percent to about 60 percent, more preferably from about 20 percent to about 50 percent, most preferably from about 30 percent to about 40 percent, of the total final weight of the particles. The appropriate amount of coating can advantageously be determined using in vitro measurements of drug release rates obtained with selected amounts of coating. The coating can be deposited by any method known to those skilled in the art, such as spray application. Spraying can be carried out by pan coating or by use of a fluid bed, such as the Wurster fluid bed described for use in depositing a drug.

After deposition of the drug, a sealant can be applied to any and/or all of the particles, prior to application of the polymeric coating. A sealant provides a physical barrier between the drug and the coating, to minimize or prevent interaction between the drug and the coating. Suitable sealants can be prepared from materials such as biologically inert, permeable, pharmaceutically acceptable polymers, such as, for example, hydroxypropylalkylcelluloses, wherein "alkyl" refers to $C_1$–$C_6$ hydrocarbon chains. Exemplary materials include hydroxypropyl methylcellulose, hydroxypropylethylcellulose, hydroxypropyl propylcellulose, and hydroxypropylbutylcellulose. Hydroxypropylmethylcellulose is preferred. While other materials are known to those skilled in the art for use as sealants, such as, for example, cellulose acetate methyl carbamate, cellulose acetate diethyl aminoacetate, semipermeable polyurethanes, semipermeable sulfonated polystyrenes, semipermeable cross-linked polymers such as poly(vinylbenzyltrimethyl)ammonium chloride, these are not preferred as they may affect the release rate of certain drugs including d-MPD. A sealant can be prepared by adding the material to water, and agitating for a time and at a rate sufficient to form a solution. The formation of a solution will be indicated, for example, by transparency and the absence of visually observable suspended material. The amount of material added to the water is not critical but is determined by viscosity. A solution which is too viscous will present difficulties in spraying. Generally, the amount of material should not exceed about 20 weight/volume percent, i.e., 20 g sealant material per 100 ml of water. Preferably, the amount of material in the water is from about 5 percent to about 15 weight/volume percent, and more preferably about 10 weight/volume percent.

Following deposition of the optional sealant and the coating, the coated particles are cured. "Curing" means that the particles are held at a controlled temperature for a time sufficient to provide stable release rates. Stability in release rate is indicated when further curing does not affect the release rate. In contrast, instability of release rate means that as the cure time is increased, the release rate continues to vary. Curing for a sufficient time ensures that substantially the same release rate is obtained with all particles of a particular size coated with a given amount of a given coating composition. A suitable curing time can be determined by one of skill in the art without undue experimentation, by noting the variability in in vitro release times as curing time is varied. As a general guideline, many formulations can be cured in about 24 hours.

Curing can be accomplished, for example, in a forced air oven. Curing can be carried out at any temperature above room temperature, "room temperature" being defined as from about 18° C. to about 25° C. Preferably, curing is carried out at a temperature of from about 30° C. to about 50° C., more preferably from about 35° C. to about 45° C., and most preferably about 40° C. Curing time can range from several hours to several days. Preferably, the coated particles are cured for at least about 24 hours, more preferably at least about 2 days, even more preferably at least about 3 days, still more preferably at least about 4 days, still even more preferably at least about 5 days, even more preferably at least about 6 days, and most preferably for about 7 days. While no significant adverse effects or advantages have been observed when the particles are cured for longer than about 7 days, it has been found that curing for less than about 24 hours may result in relatively poorer storage stability as compared to particles cured for longer periods of time.

The amount of methylphenidate drug contained in the first and second groups of particles depends upon the prescribed dosage to be delivered to a patient. The first group of particles can consist substantially entirely of a methylphenidate drug. "Substantially entirely" means that about 95 percent or more of the weight of the first group of particles can consist of a methylphenidate drug. If desired, the first group of particles can also contain pharmaceutically acceptable carriers, excipients, and other components which do not interfere with the substantially immediate release of the medication. "Substantially immediate" release, as used herein, means that at least about 90 percent of the medication is released within about 30 minutes from the time the drug is ingested. The second group of particles can contain from about 2 percent to about 75 percent, preferably from about 4 percent to about 50 percent, medication, based on the total weight of the particles including the coating to be deposited thereon.

According to the invention, a first and a second group of particles can be administered simultaneously as part of one dosage form. Any dosage form can be used. For example, the two groups of particles can be combined within a capsule. Alternatively, the two groups of particles can be pressed into a solid form such as a tablet. In pressing the particles into a solid form, suitable processing aids known to those skilled in the art can be used. Alternatively, particles coated to provide a delayed dose of a medication can be dispersed within or blended with, the medication in powder form.

As discussed, the dosage form can comprise a single group of particles providing both a substantially immediate dose of a methylphenidate drug, and a delayed dose of methylphenidate drug. The particles comprise, in admixture with one or more binders, from about 2% to about 75% by weight of a methylphenidate drug for delayed release, and a coating comprising the pharmaceutically acceptable, substantially neutral copolymers described herein. The particles further comprise, exterior to the coating, an outer layer comprising methylphenidate drug, to provide an initial, substantially immediate, dose. The substantially immediate dose is preferably released within about 30 minutes, more preferably about 15 minutes, and most preferably within about 5 minutes following ingestion. The outer layer can optionally comprise additives such as, for example, binders, excipients, and lubricants known to those skilled in the art.

The dosage forms provided by the invention can be of any shape suitable for oral administration of a drug, such as spheroidal, cube-shaped, oval, bean shaped, or ellipsoidal. The dosage form may be in the form of granules, which may be irregularly shaped. In any of the embodiments of the present invention, although the size of the particles is generally not critical, a certain particle size or sizes can be preferred depending upon the characteristics of the dosage form. For example, the dosage form can comprise a capsule containing a first and/or second group of particles. The particles should then be of a size which allows for ease in handling, and which allows for the particles comprising a desired quantity of drug to be readily measured and inserted into the capsule. If the dosage form comprises a single group of particles providing a substantially immediate dose and a delayed dose, the particles are preferably of a size and shape which facilitate oral administration. For example, the particles can be in the form of tablets, caplets, etc. Alternatively, the particles can be contained within a capsule of suitable size and shape for oral administration. If desired, various fillers and/or binders known to those skilled in the art can be included in the particles to provide the desired size and shape.

It will be recognized by one skilled in the art that the dosage forms of the present invention may include, in either or both of the first dose and any delayed dose, pharmaceutically acceptable carriers, extenders, fillers, processing aids, and excipients known to those skilled in the art.

The following examples are merely illustrative of the present invention and should not be considered limiting of the scope of the invention in any way. These examples and equivalents thereof will become more apparent to those skilled in the art in light of the present disclosure and the accompanying claims.

EXAMPLE 1

Preparation of Layered Pellets Containing d-MPD Hydrochloride

A solution of d-MPD hydrochloride was prepared as follows. To 300 grams (g) of deionized water were added 100 g of d-MPD hydrochloride, followed by moderate mixing, using a stirring paddle, for 5 minutes. A 10 percent (weight) solution of hydroxypropyl methylcellulose (HPMC E-6 from Dow Chemicals, Midland, Mich.; 250 g) was added, followed by homogenization for 5 minutes using an emulsifier head (Silverson, Chesham, UK; Model L4R). After addition of another 150 g of deionized water, the solution was sonicated for 15 minutes (Sonicor Model SC-150T; Instruments Corporation, Copiague, N.Y.), at which time the solution was clear.

A second solution was prepared by combining 300 g of deionized water and 300 g of a 10% (wt) HPMC E-6 solution and mixing for 5 minutes.

The first solution was sprayed onto 25/30 mesh non-pareil seeds (Ozone Co., Elmwood Park, N.J.) in a fluid bed apparatus (GPCG-1, Glatt Air Techniques, Inc., Ramsey, N.J.) using a Wurster head. The second solution was then sprayed to form a sealant. For both solutions, the spray rate was 8–9 g/minute. Inlet temperature was 50–55° C. and the non-pareil seeds were maintained at 35–40° C. Air volume was 6–7 meters per second (m/s).

EXAMPLE 2

Preparation of Coated Pellets Containing d-MPD Hydrochloride

A dispersion of 844 g of Eudragit® RS30D (ammoniomethacrylate copolymer from Hüls America, Somerset, N.J.; EA/MMA/TAMCl 1:2:0.1), was screened through a 60 mesh screen, then stirred for 15 minutes. A dispersion of 44 g of Eudragit® RL30D (EA/MMA/TAMCl 1:2:0.2) was similarly screened and stirred. The two dispersions were combined and stirred for 15 minutes, forming a combined dispersion. Triethyl citrate (TEC; from Moreflex, Greensboro, N.C.; 54 g) was added, followed by an additional 15 minutes of stirring. Deionized water (664 g) was added, followed by 15 minutes of stirring. Talc (108 g; from Luzenac, Englewood, Colo.) was added, followed by further stirring for 15 minutes.

The resulting combined dispersion was sprayed onto layered pellets prepared according to Example 1, using a fluid bed apparatus as used in Example 1. Spray rate was 9–10 g/minute, inlet temperature 40–45° C., and air volume 5–6 m/s. The non-pareils were maintained at 30–35° C. during spraying. A total of 960 g of dispersion was sprayed onto the pellets, representing a 30% weight increase due to the applied coating.

EXAMPLE 3

Evaluation of Drug Release Profile for Coated Pellets Prepared According to Example 2

Pellets were prepared according to Example 2, varying the ratios of the polymers between 90:10 and 93:7.

Dissolution Measurements

Dissolution was carried out in order to determine rate of release of d-MPD from the pellets. USP Apparatus I (United States Pharmacoepia Convention, Rockville, Md.) was used. The dissolution medium was 900 ml of deionized water (unless otherwise specified) and the temperature was maintained at 37° C. The sample cell size was 1 cm (a flow through cell), and the samples were stirred continuously at 100 rpm. The apparatus was equipped with a diode array spectrophotometer, and absorption at 220 nanometers (nanometers (nm)) was measured to determine the concentration of d-MPD. Samples were measured at 60, 120, 180, 240, 360, 480, 600, 720, 840, 900, 960, 1080, 1200, 1320 and 1440 minutes.

Results of the dissolution measurements are presented in Table 1. The results indicate that the amount of drug released is influenced by: amount of coating, ratio of the two polymers, amount of talc, and curing time.

EXAMPLE 4

Comparative Example

A dispersion of 911.25 g of Eudragit® RS30D was passed through a 60 mesh screen and mixed with a similarly screened dispersion of 101.25 g of Eudragit® RL30D for 15 minutes at moderate speed. Triethyl citrate (61 g) was added, followed by an additional 15 minutes of mixing. After mixing, 991.5 g of deionized water, then 61 g of talc were added with 15 additional minutes of mixing following each addition. The resulting dispersion (1600 g) was sprayed onto 800 g of layered sealed pellets prepared according to Example 1.

No delay was observed; substantially all of the drug was released within approximately one hour. Result is shown in Table 1 (Trial 1).

EXAMPLE 5

Comparative Example

A dispersion of 600 g of Eudragit® NE30D was screened through a 60 mesh screen and mixed with a 600 g dispersion of magnesium stearate for 15 minutes at moderate speed. The resulting dispersion (750 g) was sprayed onto 750 g of layered and sealed pellets prepared according to Example 1.

After a delay of 2 hours, release of the drug was observed. About 85% of the drug was released after 14 total hours.

TABLE 1

RELEASE TIMES

| Trial No. | % coat | Ratio | Delay | Talc, % | Cure time | Time for 85% release |
|---|---|---|---|---|---|---|
| 1 | 40 | 90:10 | none | 20.0 | 24 hrs | 1.0 |
| 2 | 30 | 95:5 | 4.0 | 20.0 | " | 8.0 |
| 3 | 30 | 95:5 | 4.0 | 20.0 | " | 8.0 |
| 4 | 30 | 93:7 | 1.0 | 20.0 | " | 3.0 |
| 5 | 40 | 93:7 | 1.0 | 20.0 | " | 4.0 |
| 6 | 30 | 93.5:6.5 | 2.0 | 20.0 | " | 5.0 |
| 7 | 40 | " | 2.0 | 20.0 | " | 5.0 |
| 8 | 30 | 94.5:5.5 | 2.0 | 20.0 | " | 8.0 |
| 9 | 40 | " | 1.0 | 20.0 | " | 5.0 |
| 10 | 30 | 94:6 | 2.0 | 20.0 | " | 5.0 |
| 11 | 40 | " | 2.0 | 20.0 | " | 5.0 |
| 12 | 30 | 95:5 | 2.0 | 40.0 | " | 5.0 |
| 13 | 40 | " | 3.0 | 40.0 | " | 8.0 |
| 14 | 30 | 96:4 | 4.0 | 40.0 | " | 10.0 |
| 15 | 40 | " | 5.0 | 40.0 | " | 10.0 |
| 16 | 30 | " | 4.0 | 40.0 | 7 days | 10.0 |
| 17 | 20 | 95:5 | 2.0 | 40.0 | " | 5.0 |
| 18 | 30 | " | 3.0 | 40.0 | " | 6.0 |
| 19 | 30 | " | 3.0 | 40.0 | " | 6.0 |
| 20 | 30 | " | 2.0 | 40.0 | " | 6.0 |
| 21 | 40 | " | 3.0 | 40.0 | " | 8.0 |

What is claimed:

1. A solid dosage form comprising d-threo methylphenidate or salt thereof providing a plasma concentration profile of said d-threo methylphenidate or salt thereof comprising two maxima temporally separated by from about two hours to about seven hours, said solid dosage form comprising:
   (a) a first group of particles comprising from about 2% to about 99% by weight of d-threo methylphenidate or salt thereof; and
   (b) a second group of particles comprising coated particles, said coated particles comprising from about 2% to about 75% by weight of d-threo methylphenidate or salt thereof in admixture with one or more binders and a coating comprising an ammonio methacrylate copolymer.

2. The solid dosage form of claim 1, wherein said solid dosage form is a tablet.

3. The solid dosage form of claim 1, wherein said solid dosage form is a capsule.

4. The solid dosage form of claim 1, wherein the d-threo methylphenidate or salt thereof is d-threo methylphenidate hydrochloride.

5. The solid dosage form of claim 1, wherein the first group of particles provides a substantially immediate dose of said d-threo methylphenidate upon ingestion by a mammal.

6. The solid dosage form of claim 1, wherein the magnitude of said plasma concentration profile maxima differ by no more than about 30%.

* * * * *